United States Patent
Jodele

(10) Patent No.: US 12,037,389 B2
(45) Date of Patent: Jul. 16, 2024

(54) COMPOSITIONS FOR INTERFERON BLOCKADE AND METHODS OF USING SAME

(71) Applicant: Children's Hospital Medical Center, Cincinnati, OH (US)

(72) Inventor: Sonata Jodele, Hawthorne, CA (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 320 days.

(21) Appl. No.: 16/766,327

(22) PCT Filed: Nov. 21, 2018

(86) PCT No.: PCT/US2018/062210
§ 371 (c)(1),
(2) Date: May 22, 2020

(87) PCT Pub. No.: WO2019/108456
PCT Pub. Date: Jun. 6, 2019

(65) Prior Publication Data
US 2020/0369763 A1    Nov. 26, 2020

Related U.S. Application Data

(60) Provisional application No. 62/593,401, filed on Dec. 1, 2017.

(51) Int. Cl.
| | |
|---|---|
| C07K 16/00 | (2006.01) |
| A61P 7/02 | (2006.01) |
| C07K 16/18 | (2006.01) |
| C07K 16/24 | (2006.01) |
| C12Q 1/6883 | (2018.01) |
| A61K 39/00 | (2006.01) |

(52) U.S. Cl.
CPC .............. *C07K 16/249* (2013.01); *A61P 7/02* (2018.01); *C07K 16/18* (2013.01); *C12Q 1/6883* (2013.01); *A61K 2039/507* (2013.01); *C07K 2317/21* (2013.01); *C07K 2317/24* (2013.01); *C07K 2317/76* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,355,245 B1 | 3/2002 | Evans et al. | |
| 7,700,098 B2 | 4/2010 | Ferlin et al. | |
| 8,999,340 B2 * | 4/2015 | Magro | A61K 45/06 514/56 |
| 9,447,176 B2 | 9/2016 | Rother et al. | |
| 9,494,601 B2 | 11/2016 | McKnight et al. | |
| 10,039,802 B2 | 8/2018 | Francois et al. | |
| 10,254,288 B2 | 4/2019 | Wippermann et al. | |
| 10,815,296 B2 | 10/2020 | Jodele et al. | |
| 2006/0234285 A1 | 10/2006 | Gentz et al. | |
| 2007/0116710 A1 | 5/2007 | Bell et al. | |
| 2009/0269356 A1 | 10/2009 | Epstein et al. | |
| 2011/0212900 A1 | 9/2011 | Ikezoe et al. | |
| 2012/0237515 A1 | 9/2012 | Bell et al. | |
| 2015/0174243 A1 | 6/2015 | Magro | |
| 2016/0046709 A1 | 2/2016 | Welcher et al. | |
| 2016/0300037 A1 | 10/2016 | Mould | |
| 2016/0326244 A1 * | 11/2016 | de Min | A61P 7/00 |
| 2018/0142015 A1 | 5/2018 | de Min et al. | |
| 2019/0202899 A1 | 7/2019 | Jodele et al. | |

FOREIGN PATENT DOCUMENTS

| | | | |
|---|---|---|---|
| WO | WO 2004/034988 A2 | 4/2004 | |
| WO | WO 2014/003744 A1 | 1/2014 | |
| WO | WO 2015/039126 A1 | 3/2015 | |
| WO | WO-2015039126 A1 * | 3/2015 | ............. A61P 13/12 |
| WO | WO 2015/070041 A1 | 5/2015 | |
| WO | WO 2016/200627 A1 | 12/2016 | |

OTHER PUBLICATIONS

Kavanagh et al., Blood. Dec. 15, 2016;128(24):2824-2833. doi: 10.1182/blood-2016-05-715987. Epub Sep. 23, 2016. PMID: 27663672 PMCID: PMC5159705.*
Kundra et al., Crit Rev Oncol Hematol. Apr. 2017;112:103-112. doi: 10.1016/j.critrevonc.2017.02.011. Epub Feb. 17, 2017. PMID: 28325251.*
Colburn, WA., Drug Metab Rev. 1980;11(2):223-62. doi: 10.3109/03602538008994026. PMID: 7011759.*
Bai, S., et al., "A Guide to Rational Dosing of Monoclonal Antibodies," Clin Pharmacokinet, 2012, 51(2):119-135, 17 pgs.
Dirks, N.L., et al., "Population Pharmacokinetics of Therapeutic Monoclonal Antibodies," Clin Pharmacokinet, 2010, 49(10):633-659, 27 pgs.
Mehvar, R., "Estimation of Pharmacokinetic Parameters Based on the Patient-Adjusted Population Data," American Journal of Pharmaceutical Education, 2006, 70(5):1-8, Article 96, 8 pgs.
Mould, D.R., "Why Therapeutic Drug Monitoring Is Needed for Monoclonal Antibodies and How Do We Implement This?" Clinical Pharmacology & Therapeutics, 2016, 99(4):351-354, 4 pgs.
Munnink, T.H.O., et al., "Therapeutic Drug Monitoring of Monoclonal Antibodies in Inflammatory and Malignant Disease: Translating TNF-α Experience to Oncology," Clinical Pharmacology & Therapeutics, 2016, 99(4):419-431, 13 pgs.

(Continued)

*Primary Examiner* — Michael Szperka
(74) *Attorney, Agent, or Firm* — Frost Brown Todd LLP

(57) ABSTRACT

Disclosed are compositions that may include one or more inhibitors of interferon activity for the treatment of a disease state, for example, a disorder associated with increased interferon levels such as thrombotic microangiopathy ("TMA"). Also disclosed are methods of treating an individual having a disease state such as thrombotic microangiopathy. Further disclosed are methods of diagnosing an individual with TMA.

15 Claims, 6 Drawing Sheets

(56) References Cited

OTHER PUBLICATIONS

Ghosh, S., et al., "Interfering with interferons in inflammatory bowel disease," Gut Microbiota, British Medical Assoc, 2006, 55(8):1071-1073, 3 pgs.
Khosla, J., et al., "Hematopoietic stem cell transplant-associated thrombotic microangiopathy: current paradigm and novel therapies," Bone Marrow Transplantation, 2018, 53:129-137, 9 pgs.
Kundra, A., et al., "Interferon induced thrombotic microangiopathy (TMA): Analysis and concise review," Critical Reviews in Oncology/Hematology, Elsevier, 2017, 112:103-112, 10 pgs. (XP029945081).
Kundra, A., et al., "Interferon induced thrombotic microangiopathy (TMA): Analysis and concise review," Critical Reviews in Oncology/Hematology, Science Direct, 2017, 112:103-112, 21 pgs. (XP55825262).
"Total Complete Activity," Wikipedia, downloaded Nov. 6, 2021 from https://en.wikipedia.org/w.index.php?title=Total_complement_activity&oldid=1026475679, last updated Jun. 2, 2021, 2 pgs.
European Search Report, Partial, and Provisional Written Opinion dated Jul. 28, 2021 for Application No. EP 18883814.8, 14 pgs.
European Search Report, Supplementary, and Written Opinion dated Oct. 29, 2021 for Application No. EP 18883814.8, 12 pgs.
Japanese Office Action, Notice of Reasons for Refusal, dated Aug. 2, 2021 for Application No. JP 2019-234471, 8 pgs.
Aldoss, O., et al., "Pericardial effusion after pediatric hematopoietic cell transplant," Pediatr Transplant, 2013, 17:294-299, 6 pgs.
Aljitawi, O.S., et al., "Late-Onset Intestinal Perforation in the Setting of Posttransplantation Microangiopathy: A Case Report," Transplant Proc, 2010, 42:3892-3893, 2 pgs.
Allinovi, M., et al., "Thrombotic microangiopathy induced by interferon beta in patients with multiple sclerosis: three cases treated with eculizumab," Clin Kidney J, 2017, 10(5):625-631, 7 pgs.
Anderson, B.J., et al., "Tips and traps analyzing pediatric PK data," Pediatric Anesthesia, 2011, 21:222-237, 16 pgs.
Arai, Y., et al., "Serum Neutrophil Extracellular Trap Levels Predict Thrombotic Microangiopathy after Allogeneic Stem Cell Transplantation," Biol Blood Marrow Transplant, 2013, 19:1683-1689, 7 pgs.
Au, W-Y., et al., "Successful treatment of thrombotic microangiopathy after haematopoietic stem cell transplantation with rituximab," Br J Haematol, 2007, 137:475-478, 4 pgs.
Baghbanian, S.M., et al., "Thrombotic microangiopathy associated with interferon-beta treatment in patients with multiple sclerosis," Iran J Neurol, 2018, 17(2):89-90, 2 pgs.
Baker, K. F., et al., "Novel therapies for immune-mediated inflammatory diseases: What can we learn from their use in rheumatoid arthritis, spondyloarthritis, systemic lupus erythematosus, psoriasis, Crohn's disease and ulcerative colitis?" Ann Rheum Dis, Feb. 2018, 77(2):175-187, 13 pgs.
Batts, E.D., et al., "Diagnosis and treatment of transplantation-associated thrombotic microangiopathy: real progress or are we still waiting?" Bone Marrow Transplant, 2007, 40:709-719, 11 pgs.
Bauer, R.J., et al., "A Survey of Population Analysis Methods and Software for Complex Pharmacokinetic and Pharmacodynamic Models with Examples," The AAPS Journal, 2007, 9(1)(Article7):E60-E83, 24 pgs.
Biedermann, B.C., "Vascular endothelium and graft-versus-host disease," Best Pract Res Clin Haematol, 2008; 21:129-138, 10 pgs.
Billiau, A., "Interferon-γ: Biology and Role in Pathogenesis," Adv Immunol, 1996, 62:61-130, 70 pgs.
The Binding Site Group, Ltd., CH50 Eq, Enzyme Immunoassay Kit; For in-vitro diagnostic use only; Product code: MK095, Birmingham, UK, Sep. 21, 2009, pp. 1-3, 6 pgs.
Bracaglia, C., et al. "Elevated circulating levels of interferon-γ and interferon-γ-induced chemokines characterize patients with macrophage activation syndrome complicating systemic juvenile idiopathic arthritis," Ann Rheum Dis, 2017, 76:166-172, 7 pgs.
Brukamp, K., et al., "Nephrotic Syndrome after Hematopoietic Cell Transplantation: Do Glomerular Lesions Represent Renal Graft-versus-Host Disease?" Clin J Am Soc Nephrol, 2006, 1:685-694, 10 pgs.

Carella, A.M., et al., "Rituximab for allo-SCT-associated thrombotic thrombocytopenia purpura," Bone Marrow Transplant, 2008, 41:1063-1065, 3 pgs.
Carmona, A., et al., "Distinct Deleterious Effects of Cyclosporine and Tacrolimus and Combined Tacrolimus-Sirolimus on Endothelial Cells: Protective Effect of Defibrotide," Biol Blood Marrow Transplant, 2013, 19:1439-1445, 7 pgs.
Carreras, E., et al., "The role of the endothelium in the short-term complications of hematopoietic SCT," Bone Marrow Transplant, 2011, 46:1495-1502, 8 pgs.
Cataland, S.R., et al., "Biomarkers of terminal complement activation confirm the diagnosis of aHUS and differentiate aHUS from TTP," Blood, 2014, 123(24):3733-3738, 7 pgs.
Chalandon, Y., et al., "Prevention of Veno-Occlusive Disease with Defibrotide after Allogeneic Stem Cell Transplantation," Biol Blood Marrow Transplant, 2004, 10:347-354, 8 pgs.
Chang, A., et al., "Spectrum of Renal Pathology in Hematopoietic Cell Transplantation: A Series of 20 Patients and Review of the Literature," Clin J Am Soc Nephrol, 2007. 2:1014-1023, 10 pgs.
Changsirikulchai, S., et al., "Renal Thrombotic Microangiopathy after Hematopoietic Cell Transplant: Role of GVHD in Pathogenesis," Clin J Am Soc Nephrol, 2009, 4:345-353, 9 pgs.
Chen, J., et al., "Genome-Wide Signatures of Transcription Factor Activity: Connecting Transcription Factors, Disease, and Small Molecules," PLoS Comput Biol, 2013; 9(9):e1003198, 12 pgs.
Cho, B-S., et al., "Clinical impact of thrombotic microangiopathy on the outcome of patients with acute graft-versus-host disease after allogeneic hematopoietic stem cell transplantation," Bone Marrow Transplant, 2008, 41:813-820, 8 pgs.
Cho, B-S., et al., "Validation of Recently Proposed Consensus Criteria for Thrombotic Microangiopathy After Allogeneic Hematopoietic Stem-Cell Transplantation," Transplantation, 2010, 90:918-926, 9 pgs.
Choi, C.M., et al., "Thrombotic Microangiopathy in Haematopoietic Stem Cell Transplantation: Diagnosis and Treatment," Drugs, 2009, 69:183-198, 17 pgs.
Colvin, R.B .. , "Antibody-Mediated Renal Allograft Rejection: Diagnosis and Pathogenesis," J Am Soc Nephrol, 2007, 18:1046-1056, 11 pgs.
Cooke, K.R., et al., "The Contribution of Endothelial Activation and Injury to End-Organ Toxicity Following Allogeneic Hematopoietic Stem Cell Transplantation," Biol Blood Marrow Transplant, 2008, 14:23-32, 10 pgs.
Corbacioglu, S., et al., "Defibrotide for prophylaxis of hepatic veno-occlusive disease in paediatric haemopoietic stem-cell transplantation: an open-label, phase 3, randomised controlled trial," Lancet, 2012, 379:1301-1309, 9 pgs.
Crovetto, F., et al., "The genetics of the alternative pathway of complement in the pathogenesis of HELLP syndrome," The Journal of Maternal-Fetal & Neonatal Medicine, 2012, 25:2322-2325, 5 pgs.
Cutler, C., et al., "Sirolimus and Thrombotic Microangiopathy after Allogeneic Hematopoietic Stem Cell Transplantation," Biol Blood Marrow Transplant, 2005, 11:551-557, 7 pgs.
Dandoy, C.E., et al., "Pulmonary Hypertension after Hematopoietic Stem Cell Transplantation," Biol Blood Marrow Transplant, 2013, 19:1546-1556, 11 pgs.
De Fontbrune, F.S., et al., "Use of Eculizumab in Patients with Allogeneic Stem Cell Transplant-Associated Thrombotic Microangiopathy: A Study from the SFGM-TC," Transplantation, 2015, 99(9):1953-1959, 7 pgs.
Diamedix, EZ Complement Cells—CH50 Test, for In Vitro Diagnostic Use, Product Information Sheet, dated Jan. 1, 2014, download Dec. 17, 2018 from http://diamedix.com/wp-contect/uploads/2015/10/PI-EZ-Complement-CH50-789-001Rev6-June15.pdf, 3 pgs.
Dierickx, D., et al., "Thrombotic Microangiopathy Following Intestinal Transplantation: A Single Center Experience," Transplant Proc, 2010, 42:79-81, 3 pgs.
Dietrich, S., et al., "Endothelial Vulnerability and Endothelial Damage Are Associated with Risk of Graft-versus-Host Disease and Response to Steroid Treatment," Biol Blood Marrow Transplant, 2013, 19:22-27, 6 pgs.

(56) References Cited

OTHER PUBLICATIONS

Eremina V, et al., "VEGF Inhibition and Renal Thrombotic Microangiopathy," N Engl J Med, 2008, 358:1129-1136, 12 pgs.

Essaghir, A., et al., "Transcription factor regulation can be accurately predicted from the presence of target gene signatures in microarray gene expression data," Nucleic Acids Research, 2010, 38(11):e120, 11 pgs.

Falkner, B., et al., "Summary of the Fourth Report on the Diagnosis, Evaluation, and Treatment of High Blood Pressure in Children and Adolescents," Hypertension, 2004, 44:387-388, 2 pgs.

Feng, S., et al., "Partial ADAMTS13 deficiency in atypical hemolytic uremic syndrome," Blood, 2013, 122:1487-1493, 7 pgs.

Fuge, R., et al., "The clinical features, risk factors and outcome of thrombotic thrombocytopenia purpura occurring after bone marrow transplantation," Br J Haematol, 2001, 113:58-64, 7 pgs.

Fujino M, et al., "Intestinal thrombotic microangiopathy induced by FK506 in rats," Bone Marrow Transplant, 2007, 39:367-372, 6 pgs.

Furie, R., et al. "Anifrolumab, an Anti-Interferon-α Receptor Monoclonal Antibody, in Moderate-to-Severe Systemic Lupus Erythematosus" Arthritis & Rheumatology, 2017, 69(2):376-386, 11 pgs.

Galie, N., et al., "Guidelines for the Diagnosis and Treatment of Pulmonary Hypertension: The Task Force for the Diagnosis and Treatment of Pulmonary Hypertension of the European Society of Cardiology (ESC) and the European Respiratory Society (ERS), endorsed by the International Society of Heart and Lung Transplantation (ISHLT)," European Heart Journal, 2009, 30:2493-2537, 45 pgs.

Gatault, P., et al., "Therapeutic drug monitoring of eculizumab: Rationale for an individualized dosing schedule," mAbs, 2015, 7(6):1205-1211, 7 pgs.

George, J.N., et al., "Thrombotic microangiopathy after allogeneic bone marrow transplantation: a pathologic abnormality associated with diverse clinical syndromes," Bone Marrow Transplantation, 2004, 33(11):1073-1074, 2 pgs.

George, J.N., et al., "Thrombotic thrombocytopenia purpura-hemolytic uremic syndrome following allogeneic HPC transplantation: a diagnostic dilemma," Transfusion, 2004, 44:294-304, 11 pgs.

Glezerman IG, et al., "Chronic Kidney Disease, Thrombotic Microangiopathy, and Hypertension Following T Cell-Depleted Hematopoietic Stem Cell Transplantation," Biol Blood Marrow Transplant, 2010, 16:976-984, 9 pgs.

Gloude, N.J., et al., "Endothelial Injury, Neutrophil Extracellular Traps, and Complement Activation in Thrombotic Microangiopathy and GVHD," Abstracts / Biology of Blood and Marrow Transplantation, 2017, 23(3):S232-S233, Abstract 310, 2 pgs.

Gloude, N.J., et al., "Thrombotic Microangiopathy Can Occur Before Transplant in Children with HLH," Abstracts / Biology of Blood and Marrow Transplantation, 2017, 23(3):S233-S234, Abstract 311, 2 pgs.

Goodwin, J.E., et al., "Glucocorticoid-induced hypertension," Pediatr Nephrol, 2012, 27:1059-1066, 8 pgs.

Gooley, T.A., et al., "Reduced Mortality after Allogeneic Hematopoietic-Cell Transplantation," N Engl J Med, 2010, 363:2091-2101, 11 pgs.

Gralwohl, A., et al., "Current trends in hematopoietic stem cell transplantation in Europe," Blood, 2002, 100(7):2374-2386, 14 pgs.

Haines, H.L., et al., "Blood, and Not Urine, BK Viral Load Predicts Renal Outcome in Children with hemorrhagic Cystitis Following Hematopoietic Stem Cell Transplantation," Biol Blood Marrow Transplant, 2011, 17:1512-1519, 8 pgs.

Hale, G.A., et al., "Hemolytic Uremic Syndrome after Bone Marrow Transplantation: Clinical Characteristics and Outcome in Children," Biol Blood Marrow Transplant, 2005, 11:912-920, 9 pgs.

Health Resources and Services Administration (HRSA), US Department of Health and Human Services, "Transplant Activity Report," Apr. 15, 2017, 3 pgs.

Hewamana, S., et al., "Intestinal perforation secondary to haematopoietic stem cell transplant associated thrombotic microangiopathy," Eur J Haematol, 2009, 83:277, 1 pg.

Hillmen, P., et al., "Effect of Exulizumab on Hemolysis and Transfusion Requirements in Patients with Paroxysmal Nocturnal Hemoglobinuria," The New England Journal of Medicine, 2004, 350(6):552-559, 8 pgs.

Hingorani, S, et al., "Urinary cytokines after HCT: evidence for renal inflammation in the pathogenesis of proteinuria and kidney disease," Bone Marrow Transplant, 2014, 49:403-409, 7 pgs.

Hingorani, S., "Chronic kidney disease after liver, cardiac, lung, heart-lung, and hematopoietic stem cell transplant," Pediatr Nephrol, 2008; 23:879-888, 10 pgs.

Hingorani, S.R., et al., "Albuminuria in Hematopoietic Cell Transplantation Patients: Prevalence, Clinical Associations, and Impact on Survival," Biol Blood Marrow Transplant, 2008, 14:1365-1372, 8 pgs.

Hiroshima Medical Association "Importance of measuring blood concentration of drugs: Basic knowledge of TDM (monitoring)," Hiroshima, Japan, May 15, 2011, No. 542, pp. 2-5, 9 pgs.

Ho, V.T., et al., "Blood and Marrow Transplant Clinical Trials Network Toxicity Committee Consensus Summary: Thrombotic Microangiopathy after Hematopoietic Stem Cell Transplantation," Biol Blood Marrow Transplant, 2005, 11:571-575, 5 pgs.

Hoffmeister, P.A., et al., "Hypertension in Long-Term Survivors of Pediatric Hematopoietic Cell Transplantation," Biol Blood Marrow Transplant, 2010, 16:515-524, 10 pgs.

Holmes, L.V., et al., "Determining the Population Frequency of the CFHR3/CFHRI Deletion at 1q32," PloS One, 2013, 8(4):e60352, 7 pgs.

Horiuchi, T., et al., "Complement-targeted therapy: development of C5- and C5a-targeted inhibition," Inflammation and Regeneration, 2016, 36:11, 5 pgs.

Houtchens, J., et al., "Diagnosis and Management of Pulmonary Arterial Hypertension," Pulmonary Medicine, 2011, 2011:845-864, 14 pgs.

Imhof, B.A., et al., "Angiogenesis and inflammation face off," Nature Medicine, 2006, 12:171-172, 2 pgs.

Inamoto, Y., et al., "Clinicopathological manifestations and treatment of intestinal transplant-associated microangiopathy," Bone Marrow Transplant, 2009, 44:43-49, 7 pgs.

Inker, L.A., et al., "Estimating Glomerular Filtration Rate from Serum Creatinine and Cystatin C," N Engl J Med, 2012, 367:20-29, 15 pgs.

Ishikawa, Y., et al., "Transplantation-associated thrombotic microangiopathy after steroid pulse therapy for polyserositis related to graft-versus-host disease," Clin Exp Nephrol, 2011, 15:179-183, 5 pgs.

Jia, H., et al., "Endothelial cell functions impaired by interferon in vitro: Insights into the molecular mechanism of thrombotic microangiopathy associated with interferon therapy," Thromb Res, 2018, 163:105-116, 12 pgs.

Jodele, S., et al., "A new paradigm: Diagnosis and management of HSCT-associated thrombotic microangiopathy as a multi-system endothelial injury," Blood Rev, 2015, 29(3):191-204, 37 pgs.

Jodele S., et al., "Abnormalities in the alternative pathway of complement in children with hematopoietic stem cell transplant-associated thrombotic microangiopathy," Blood, 2013, 122:2003-2007, 6 pgs.

Jodele, S., et al., "Diagnostic and risk criteria for HSCT-associated thrombotic microangiopathy: a study in children and young adults," Blood, 2014, 124:645-653, 9 pgs.

Jodele, S., et al., "Does early initiation of therapeutic plasma exchange improve outcome in pediatric stem cell transplant-associated thrombotic microangiopathy?" Transfusion, 2013, 53:661-667, 8 pgs.

Jodele S, et al., "Eculizumab Therapy in Children with Severe Hematopoietic Stem Cell Transplantation-Associated Thrombotic Microangiopathy," Biol Blood Marrow Transplant, 2014, 20(4):518-525, 8 pgs.

Jodele, S., et al., "Pulmonary Arterial Hypertension in Pediatric Patients with Hematopoietic Stem Cell Transplant-Associated Thrombotic Microangiopathy," Biol Blood Marrow Transplant, 2013, 19:202-207, 6 pgs.

(56) References Cited

OTHER PUBLICATIONS

Jodele, S., et al., "Successful early intervention for hyperacute transplant-associated thrombotic microangiopathy following pediatric hematopoietic stem cell transplantation," Pediatr Transplant, 2012, 16:E39-E42, 4 pgs.

Jodele, S., et al., "The genetic fingerprint of susceptibility for transplant-associated thrombotic microangiopathy," Blood, 2016, 127:989-996, 8 pgs.

Jodele, S., et al., "Variable eculizumab clearance requires pharmacodynamic monitoring to optimize therapy for thrombotic microangiopathy after hemotopoietic stem cell transplantation," Biol Blood Marrow Transplant, 2016, 22(2):307-315, 29 pgs.

Kanehisa, M., et al., KEGG: new perspectives on genomes, pathways, diseases and drugs, Nucleic Acids Research, 2017, 45:D353-D361, 9 pgs.

Keating, G.M., "Eculizumab: A Review of Its Use in Atypical Haemolytic Uraemic Syndrome," Drugs, 2013, 73:2053-2066, 14 pgs.

Keir, L., et al., "Advances in our understanding of the pathogenesis of glomerular thrombotic microangiopathy," Pediatr Nephrol, 2011, 26:523-533, 11 pgs.

Kersting, S., et al., "Acute renal failure after allogeneic myeloablative stem cell transplantation: retrospective analysis of incidence, risk factors and survival," Bone Marrow Transplant, 2007, 39:359-365, 7 pgs.

Kielstein, J.T., et al., "Best supportive care and therapeutic plasma exchange with or without eculizumab in Shiga-toxin-producing *E. coli* O104:H4 induced haemolytic-uraemic syndrome: an analysis of the German STEC-HUS registry," Nephrol Dial Transplant, 2012, 27:3807-3815, 9 pgs.

Kim, S.S., et al., "Hematopoietic stem cell transplant-associated thrombotic microangiopathy: review of pharmacologic treatment options," Transfusion, 2015, 55:452-458, 7 pgs.

Kojouri, K., et al., "Thrombotic microangiopathy following allogeneic hematopoietic stem cell transplantation," Curr Opin Oncol, 2007, 19:148-154, 7 pgs.

Kurniati, N.F., et al., "Pleiotropic effects of angiopoietin-2 deficiency do not protect mice against endotoxin-induced acute kidney injury," Nephrol Dial Transplant, 2013, 28:567-575, 9 pgs.

Labrador, J., et al., "Risk factors for thrombotic microangiopathy in allogeneic hematopoietic stem cell recipients receiving GVHD prophylaxis with tacrolimus plus MTX or sirolimus," Bone Marrow Transplant, 2014, 49(5):684-690, 7 pgs.

Lapeyraque, A.L., et al., "Eculizumab in Severe Shiga-Toxin-Associated HUS," N Engl J Med, 2011, 364:2561-2563, 3 pgs.

Laskin, B.L., et al., "Cystatin C-estimated Glomerular Filtration Rate in Pediatric Autologous Hematopoietic Stem Cell Transplantation," Biol Blood Marrow Transplant, 2012, 18:1745-1752, 8 pgs.

Laskin, B.L., et al., "Early clinical indicators of transplant-associated thrombotic microangiopathy in pediatric neuroblastoma patients undergoing auto-SCT," Bone Marrow Transplant, 2011, 46:682-689, 8 pgs.

Laskin, B.L., et al., "Renal Arteriolar C4d Deposition: A Novel Characteristic of Hematopoietic Stem Cell Transplantation-Associated Thrombotic Microangiopathy," Transplantation, 2013, 96(2):217-223, 15 pgs.

Laskin, B.L., et al., "Small vessels, big trouble in the kidneys and beyond: hematopoietic stem cell transplantation-associated thrombotic microangiopathy," Blood, 2011, 118:1452-1162, 12 pgs.

Legendre, C.M., et al., "Eculizumab in Atypical Hemolytic-Uremic Syndrome," N Engl J Med, 2013, 369:1377-1380, 4 pgs.

Legendre, C.M., et al., "Terminal Complement Inhibitor Eculizumab in Atypical Hemolytic-Uremic Syndrome," N Engl J Med, 2013, 368:2169-2181, 13 pgs.

Lerner, D., et al., "Pericardial effusion in pediatric SCT recipients with thrombotic microangiopathy," Bone Marrow Transplant, 2014, 49(6):862-863, 2 pgs.

Licht, C., et al., "Successful Plasma Therapy for Atypical Hemolytic Uremic Syndrome Caused by Factor H Deficiency Owing to a Novel Mutation in the Complement Cofactor Protein Domain 15," Am J Kidney Dis, 2005, 45:415-421, 7 pgs.

Lopes DA Silva, R., et al., "BK virus encephalitis with thrombotic microangiopathy in an allogeneic hematopoietic stem cell transplant recipient," Transpl Infect Dis, 2011, 13:161-167, 8 pgs.

Lovric, S., et al., "Removal of elevated circulating angiopoietin-2 by plasma exchange—A pilot study in critically ill patients with thrombotic microangiopathy and anti-glomerular basement membrane disease," Thrombosis and Haemostasis, 2010, 104:1038-1043, 6 pgs.

Magro, C.M., et al., "Degos Disease: A C5b-9/Interferon-α—Mediated Endotheliopathy Syndrome" Am J Clin Pathol, 2011, 135:599-610, 12 pgs.

Marr, H., et al., "Successful treatment of transplant-associated microangiopathy with rituximab," N Z Med J, 2009, 122:72-74, 3 pgs.

Martinez, M.T., et al., "Transplant-associated microangiopathy (TAM) in recipients of allogeneic hematopoietic stem cell transplants," Bone Marrow Transplant, 2005, 36:993-1000, 8 pgs.

McKeage, K., "Eculizumab: A Review of Its Use in Paroxysmal Nocturnal Haemoglobinuria," Drugs, 2011, 71:2327-2345, 19 pgs.

Menne, J., et al., "Validation of treatment strategies for enterohaemorrhagic *Escherichia coli* O104:H4 induced haemolytic uraemic syndrome: case-control study," BMJ, 2012, 345:e4565, 13 pgs.

Meri, S., "Complement activation in diseases presenting with thrombotic microangiopathy," European Journal of Internal Medicine, 2013, 24:496-502, 7 pgs.

Mii, A., et al. "Renal thrombotic microangiopathy associated with chronic humoral graft versus host disease after hematopoietic stem cell transplantation," Pathol Int, 2011, 61:34-41, 8 pgs.

Mii, A., et al., "Renal thrombotic microangiopathy associated with chronic graft-versus-host disease after allogeneic hematopoietic stem cell transplantation," Pathol Int, 2011, 61:518-527, 10 pgs.

Milan, A., et al., "Echocardiographic Indexes for the Non-Invasive Evaluation of Pulmonary Hemodynamics," J Am Soc Echocardiogr, 2010, 23:225-239, 15 pgs.

Mohammed, J., et al., "Cardiac tamponade in diarrhoea-positive haemolytic uraemic syndrome," Nephrol Dial Transplant, 2009, 24:679-681, 3 pgs.

Moulder, J.E., et al., "Captopril and Losartan for Mitigation of Renal Injury Caused by Single-Dose Total-Body Irradiation," Radiation Research, 2011, 175:29-36, 8 pgs.

Nadasdy, T., "Thrombotic microangiopathy in renal allografts: the diagnostic challenge," Curr Opin Organ Transplant, 2014, 19(3):283-292, 10 pgs.

Naina, H.V.K., et al., "Thrombotic Microangiopathy During Peripheral Blood Stem Cell Mobilization," J Clin Apher, 2009, 24:259-261, 3 pgs.

Nakamae, H., et al., "Risk Factor Analysis for Thrombotic Microangiopathy after Reduced-Intensity or Myeloablative Allogeneic Hematopoietic Stem Cell Transplantation," Am J Hematol, 2006, 81:525-531, 7 pgs.

Nakamura, Y., et al., "Nephrotic syndrome associated with thrombotic microangiopathy following allogeneic stem-cell transplantation for myelodysplastic syndrome," Br J Haematol, 2007, 136:857-859; 3 pgs.

Narimatsu, H., et al., "Intestinal thrombotic microangiopathy following reduced-intensity umbilical cord blood transplantation," Bone Marrow Transplant, 2005, 36:517-523, 7 pgs.

Nehus, E.J., et al., "Performance of cystatin C-based equations in a pediatric cohort at high risk of kidney injury," Pediatr Nephrol, 2013, 28:453-461, 9 pgs.

Nishida, T., et al., "Intestinal thrombotic microangiopathy after allogeneic bone marrow transplantation: A clinical imitator of acute enteric graft-versus-host disease," Bone Marrow Transplant, 2004, 33:1143-1150, 8 pgs.

Noris, M., et al., "Atypical Hemolytic-Uremic Syndrome," N Engl J Med, 2009, 361:1676-1687, 12 pgs.

Noris, M., et al., "STEC-HUS, atypical HUS and TTP are all diseases of complement activation," Nature Reviews Nephrology, 2012, 8:622-633, 12 pgs.

(56) References Cited

OTHER PUBLICATIONS

Norkin, M., et al., "Large pericardial effusion as a complication in adults undergoing SCT," Bone Marrow Transplant, 2011, 46:1353-1356, 4 pgs.
O'Donnell, P.H., et al., "BK Virus Infection Is Associated with Hematuria and Renal Impairment in Recipients of Allogeneic Hematopoetic Stem Cell Transplants," Biol Blood Marrow Transplant, 2009, 15:1038-1048, 12 pgs.
Orth, D., et al., "Shiga Toxin Activates Complement and Binds Factor H: Evidence for an Active Role of Complement in Hemolytic Uremic Syndrome," J Immunol, 2009, 182:6394-6400, 7 pgs.
Pachlopnik Schmid, J., et al., "Neutralization of IFNγ defeats haemophagocytosis in LCMV-infected perforin- and Rab27a-deficient mice," EMBO Mol Med, 2009, 1:112-124, 13 pgs.
Parikh, C.R., et al., "Acute renal failure independently predicts mortality after myeloablative allogeneic hematopoietic cell transplant," Kidney Int, 2005, 67:1999-2005, 8 pgs.
Passweg, J.R., et al., "Hematopoietic stem cell transplantation in Europe 2014: more than 40,000 transplants annually," Bone Marrow Transplantation, 2016, 51:786-792, 7 pgs.
Peffault De Latour, R., et al., "Assessing complement blockade in patients with paroxysmal nocturnal hemoglobinuria receiving eculizumab," Blood, 2015, 125:775-783, 9 pgs.
Peffault De Latour, R., et al., "Successful use of eculizumab in a patient with post-transplant thrombotic microangiopathy," Br J Haematol, 2013, 161:279-298, 2 pgs.
Perkowska-Ptasinska, A., et al., "Thrombotic Nephropathy and Pulmonary Hypertension Following Autologous Bone Marrow Transplantation in a Patient With Acute Lymphoblastic Leukemia: Case Report," Transplant Proc, 2006, 38:295-296, 2 pgs.
Peyvandi, F., et al., "Prospective study on the behaviour of the metalloprotease ADAMTS13 and of von Willebrand factor after bone marrow transplantation," Br J Haematol, 2006, 134:187-195, 9 pgs.
Pio, R.., et al., "Complement inhibition: a promising concept for cancer treatment," Semin Immunol, 2013, 25(1):54-64, 27 pgs.
Piscitelli, D., et al., "Unusual Case Report of Thrombotic Microangiopathy of the Small Bowel Following Liver Transplantation, a Possible Immunosuppressant-Induced Disease with Histological and Ultrastructural Findings," The Scientific World Journal, 2009, 9:1031-1034, 5 pgs.
Platzbecker, U., et al., "Graft-versus-Host disease Prophylaxis with Everolimus and Tacrolimus Is Associated with a High Incidence of Sinusoidal Obstruction Syndrome and Microangiopathy: Results of the EVTAC Trial," Biol Blood Marrow Transplant, 2009, 15:101-108, 8 pgs.
Prasad, K., et al., "Prevention of bacterial meningitis: An overview of Cochrane systematic reviews," Respiratory Medicine, 2007, 101:2037-2043, 7 pgs.
Rabinovitch, M., "Molecular pathogenesis of pulmonary arterial hypertension," The Journal of Clinical Investigation, 2012, 122(12):4306-4313, 9 pgs.
Rachakonda, S.P., et al., "Single-Nucleotide Polymorphisms Within the Thrombomodulin Gene (*THBD*) Predict Mortality in Patients with Graft-Versus-Host Disease," J Clin Oncol, 2014, 32(30):3421-3427, 9 pgs.
Rajpal, J.S., et al., "Improved Survival over the Last Decade in Pediatric Patients Requiring Dialysis after Hematopoietic Cell Transplantation," Biol Blood Marrow Transplant, 2013, 19:661-665, 5 pgs.
Reti, M., et al., "Complement activation in thrombotic thrombocytopeniaurpura," Journal of Thrombosis and Haemostasis: JTH, 2012, 10:791-798, 8 pgs.
Richardson, P.G., et al., "Defibrotide for the Treatment of Severe Hepatic Veno-Occlusive Disease and Multiorgan Failure after Stem Cell Transplantation: A Multicenter, Randomized, Dose-Finding Trial," Biol Blood Marrow Transplant, 2010, 16:1005-1017, 13 pgs.
Ricklin, D., et al., "Complement in Immune and Inflammatory Disorders: Pathophysiological Mechanisms," J Immunol, 2013, 190:3831-3838, 8 pgs.

Ricklin, D., et al., "TMA: beware of complements," Blood, 2013, 122:1997-1999, 3 pgs.
Riggs, J.M., et al., "Characterisation of anifrolumab, a fully human anti-interferon receptor antagonist antibody for the treatment of systemic lupus erythematosus," Lupus Science & Medicine, 2018, 5:e000261, 11 pgs.
Rodriguez, R., et al., "A phase II pilot study of tacrolimus/sirolimus GVHD prophylaxis for sibling donor hematopoietic stem cell transplantation using 3 conditioning regimens," Blood, 2010, 115:1098-1105, 9 pgs.
Rosenthal, J., et al., "Transplant-associated thrombotic microangiopathy in pediatric patients treated with sirolimus and tacrolimus," Pediatr Blood Cancer, 2011, 57:142-146, 10 pgs.
Roth, C., et al., "The posterior reversible encephalopathy syndrome: what's certain, what's new?" Practical Neurology, 2011, 11:136-144, 9 pgs.
Ruutu, T., et al., "Diagnostic criteria for hematopoietic stem cell transplant-associated microangiopathy: results of a consensus process by an International Working Group," Haematologica, 2007, 92:95-100, 6 pgs.
Sadeghi, B., et al., "Early-phase GVHD gene expression profile in target versus non-target tissues: kidney, a possible target?" Bone Marrow Transplant, 2013, 48:284-293, 10 pgs.
Sagrista-Sauleda, J., et al., "Diagnosis and management of pericardial effusion," World Journal of Cardiology, 2011, 3:135-143, 9 pgs.
San, T., et al., "Protective Effect of Defibrotide on Perfusion Induced Endothelial Damage," Thrombosis Research, 2000, 99:335-341, 7 pgs.
Schmidtko, J., et al., "Treatment of Atypical Hemolytic Uremic Syndrome and Thrombotic Microangiopathies: A Focus on Eculizumab," Am J Kidney Dis, 2013, 61:289-299, 11 pgs.
Schoenborn, J.R., et al., "Regulation of Interferon-γ During Innate and Adaptive Immune Responses," Chapter 2, Adv Immunol, 2007, 96:41-101, 61 pgs.
Schroder, H., "Defibrotide Protects Endothelial Cells, but not L929 Tumour Cells, from Tumour Necrosis Factor-a-mediated Cytotoxicity," J Pharm Pharmacol, 1995, 47:250-252, 3 pgs.
Schwartz, G.J., et al., "Glomerular filtration rate measurement and estimation in chronic kidney disease," Pediatr Nephrol, 2007, 22:1839-1848, 10 pgs.
Schwimmer, J., et al., "De Novo Thrombotic Microangiopathy in Renal Transplant Recipients: A Comparison of Hemolytic Uremic Syndrome With Localized Renal Thrombotic Microangiopathy," Am J Kidney Dis, 2003, 41:471-479, 9 pgs.
Shah, N., et al., "Role of ADAMTS13 in the management of thrombotic microangiopathies including thrombotic thrombocytopenia purpura (TTP)," Br J Haematol, 2013, 163:514-519, 6 pgs.
Shayani, S., et al., "Thrombotic Microangiopathy Associated with Sirolimus Level after Allogeneic Hematopoietic Cell Transplantation with Tacrolimus/Sirolimus-Based Graft-versus-Host Disease Prophylaxis," Biol Blood Marrow Transplant, 2013, 19:298-304, 7 pgs.
Siami, K., et al., "Thrombotic Microangiopathy After Allogeneic Hematopoietic Stem Cell Transplantation: An Autopsy Study," Transplantation, 2008, 85:22-28, 7 pgs.
Song, D., et al., "The spectrum of renal thrombotic microangiopathy in lupus nephritis," Arthritis Research & Therapy, 2013, 15:R12, 12 pgs.
Spector, J.T., et al., "Associations of blood lead with estimated glomerular filtration rate using MDRD, CKD-EPI and serum cystatin C-based equations," Nephrol Dial Transplant, 2011, 26:2786-2792, 8 pgs.
Staykov, D., et al., "Posterior Reversible Encephalopathy Syndrome," Journal of Intensive Care Medicine, 2012, 27:11-24, 14 pgs.
Subramanian, A., et al., "Gene set enrichment analysis: a knowledge-based approach for interpreting genome-wide expression profiles," PNAS, 2005, 102:15545-15550, 6 pgs.
Sucak, G.T., et al., "Treatment of Sinusoidal Obstruction Syndrome With Defibrotide: A Single-Center Experience," Transplant Proc, 2007, 39:1558-1563, 6 pgs.

(56) References Cited

OTHER PUBLICATIONS

Takatsuka, H., et al., "Complications after bone marrow transplantation are manifestations of systemic inflammatory response syndrome," Bone Marrow Transplant, 2000, 26:419-426, 8 pgs.
Tati, R., et al., "Complement Activation Associated with ADAMTS13 Deficiency in Human and Murine Thrombotic Microangiopathy," J Immunol, 2013, 191:2184-2193, 11 pgs.
Thurman, J.M., et al., "Alternative Pathway of Complement in Children with Diarrhea-Associated Hemolytic Uremic Syndrome," Clin J Am Soc Nephrol, 2009, 4:1920-1924, 5 pgs.
Tichelli, A., et al., "Vascular endothelium as 'novel' target of graft-versus-host disease," Best Pract Res Clin Haematol, 2008, 21(2):139-148, 10 pgs.
Tokunaga, R., et al., " CXCL9, CXCL10, CXCL11/CXCR3 axis for immune activation—a target for novel cancer therapy," Cancer Treat Rev, 2018, 63:40-47, 19 pgs.
Totina, A., et al., "Atypical Hemolytic-Uremic Syndrome in a Child Presenting With Malignant Hypertension," Clinical Pediatrics, 2013, 52:183-186, 5 pgs.
Tsai, H.M., "Untying the Knot of Thrombotic Thrombocytopeniaurpura and Atypical Hemolytic Uremic Syndrome," Am J Med, 2013, 126:200-209, 10 pgs.
Uderzo, C., et al., "Impact of thrombotic thrombocytopenia purpura on leukemic children undergoing bone marrow transplantation," Bone Marrow Transplant, 2000, 26:1005-1009, 5 pgs.
Uderzo, C., et al., "Risk Factors and Severe Outcome in Thrombotic Microangiopathy After Allogeneic Hematopoietic Stem Cell Transplantation," Transplantation, 2006, 82:638-644, 7 pgs.
Ueda, N., et al., "Predictive Value of Circulating Angiopoietin-2 for Endothelial Damage-Related Complications in Allogeneic Hematopoietic Stem Cell Transplantation," Biol Blood Marrow Transplant, 2014, 20:1335-1340, 6 pgs.
Van Den Born, B-J., et al., "Association Between Thrombotic Microangiopathy and Reduced ADAMTS13 Activity in Malignant Hypertension," Hypertension, 2008, 51:862-866, 15 pgs.
Van Der Plas, R.M., et al., "von Willebrand Factor Proteolysis is Deficient in Classic, but not in Bone Marrow Transplantation-Associated, Thrombotic Thrombocytopenia Purpura," Blood, 1999, 93:3798-3802, 6 pgs.
Waters, A.M., et al. "aHUS caused by complement dysregulation: new therapies on the horizon," Pediatr Nephrol, 2011, 26:41-57, 17 pgs.
Willems, E., et al., "Comparison of thrombotic microangiopathy after allogeneic hematopoietic cell transplantation with high-dose or nonmyeloablative conditioning," Bone Marrow Transplant, 2010, 45:689-693, 5 pgs.
Worel, N., et al., "ABO-incompatible allogeneic hematopoietic stem cell transplantation following reduced-intensity conditioning: Close association with transplant-associated microangiopathy," Transfus Apher Sci, 2007, 36:297-304, 8 pgs.
Wuhl, E., et al., "Strict Blood-Pressure Control and Progression of Renal Failure in Children," N Engl J Med, 2009, 361:1639-1650, 12 pgs.
Xu, X-J., et al., "Diagnostic Accuracy of a Specific Cytokine Pattern in Hemophagocytic Lymphohistiocytosis in Children," J Pediatr, 2012, 160:984-990, 8 pgs.
Yamada-Fujiwara, M., et al., "Diagnosis of Intestinal Graft-versus-Host Disease and Thrombotic Microangiopathy after Allogeneic Stem Cell Transplantation," Tohoku J Exp Med, 2012, 227:31-37, 8 pgs.
Youden, W.J., "Index for Rating Diagnostic Tests," Cancer, 1950, 3:32-35, 4 pgs.
Zhang, S-Y., et al. "Inborn errors of interferon (IFN)-mediated immunity in humans: insights into the respective roles of IFN-$\alpha/\beta$, IFN-$\gamma$, and IFN-$\lambda$ in host defense," Immunol Rev, 2008, 226:29-40, 12 pgs.
Zheng, S., et al., "Model-Based Assessment of Dosing Strategies in Children for Monoclonal Antibodies Exhibiting Target-Mediated Drug Disposition," CPT Pharmacometrics Syst Pharmacol, 2014, 3:e138, 10 pgs.

Canadian Office Action dated Jan. 25, 2017 for Application No. CA 2,921,856, 4 pgs.
Canadian Office Action dated Feb. 8, 2018 for Application No. CA 2,921,856, 4 pgs.
Canadian Office Action dated Nov. 30, 2018 for Application No. CA 2,921,856, 5 pgs.
Extended European Search Report and Opinion dated Mar. 20, 2017 for Application No. EP 14843902.9, 9 pgs.
European Exam Report dated Jan. 25, 2018 for Application No. 14843902.9, 4 pgs.
European Office Action, Summons to attend oral proceedings pursuant to Rule 115(1) EPC, dated Jan. 16, 2019 for Application No. EP 14843902.9, 18 pgs.
European Search Report, Extended, and Written Opinion dated Nov. 12, 2020 for Application No. EP 20164737.7, 11 pgs.
European Search Report, Supplementary, and Written Opinion dated Dec. 17, 2018 for Application No. EP 1680827.3, 8 pgs.
International Search Report and Written Opinion dated Dec. 31, 2014 for Application No. PCT/US2014/055922, 12 pgs.
International Search Report and Written Opinion dated Sep. 9, 2016 for Application No. PCT/US2016/034547, 10 pgs.
International Search Report and Written Opinion dated Feb. 7, 2019 for Application No. PCT/US2018/062210, 12 pgs.
Japanese Office Action dated Nov. 30, 2018 for Application No. 2016-542879, 6 pgs.
Japanese Office Action dated Nov. 30, 2018 for Application No. 2016-542879, 9 pgs. English Translation.
Japanese Office Action, Notice of Reasons for Refusal, dated Sep. 26, 2019 for Application No. JP 2016-542879, 8 pgs.
U.S. Appl. No. 61/878,119, filed Sep. 16, 2013, by Jodele, entitled: "Optimal management of eculizumab therapy based on pharmacodynamic marker in children treated for hematopoietic stem cell transplantation-associated thrombotic microangiopathy."
U.S. Appl. No. 62/172,987, filed Jun. 9, 2015, by Jodele, et al., entitled: "Dosing Algorithm for Eculizumab.".
U.S. Appl. No. 62/593,401, filed Dec. 1, 2017, by Jodele, entitled: "Interferon pathway blockade to treat endothelial injury and thrombotic microangiopathies."
Sperati, C.J., "Thrombotic Microangiopathy: What is it?" Johns Hopkins Medicine, Division of Nephrology, 2022, downloaded from https://www.hopkinsmedicine.org/nephrology/tm_sperati#:~:text= What%20is%20it%3F.in%20capillaries%20and%20small% 20arteries, 4 pgs.
Japanese Office Action, Decision of Dismissal of Amendment, dated Jun. 13, 2022 for Application No. JP 2019-234471, 2 pgs.
Japanese Office Action, Decision of Refusal, dated Jun. 13, 2022 for Application No. JP 2019- 234471, 4 pgs.
Japanese Office Action, Notice of Reasons for Refusal, dated Jan. 11, 2023 for Application No. JP 2022-014712, 2 pgs.
Barnett, A.N.R., et al., "The use of eculizumab in renal transplantation," Clin Transplant, 2013, 27:E2016-E229, 15 pgs.
Benet, L.Z., et al., "Basic Principles of Pharmacokinetics," Toxicologic Pathology, 1995, 23(2):115-123, 9 pgs.
Gloude, N.J., et al., "Thinking Beyond HLH: Clinical Features of Patients with Concurrent Presentation of Hemophagocytic Lymphohistiocytosis and Thrombotic Microangiopathy," J Clin Immunol, 2020, 40(5):699-707, 9 pgs.
Soliris© (eculizumab), Highlights of Prescribing Information, 2011 rev., pp. 1-24, 24 pgs.
Wolff, K., "Pharmacokinetics," In: Encyclopedia of Psychopharmacology, Stolerman, I.P, and Price, L.H. (eds.) Springer, Berlin, Heidelberg, 2015, pp. 1200-1415, 217 pgs.
Mizuno, K., et al., "Integration of Pharmacodynamic Biomarker with Modeling & Simulation for Eculizumab Precision Dosing in Pediatric Patients with Hematopoietic Stem Cell Transplant Associated-Thrombotic Microangiopathy," Abstracts from the 11th American Conference of Pharmacometrics (ACoP11), vol. 2, Nov. 9-13, 2020, TUE-045, ISSN:2688-3953, XP093033648, 3 pgs.
International Search Report and Written Opinion dated Apr. 3, 2023 for Application No. PCT/US2022/053603, 9 pgs.

(56) References Cited

OTHER PUBLICATIONS

Japanese Office Action, Reconsideration Report by Examiner before Appeal, dated Jan. 4, 2023 for Application No. JP 2019-234471, Appeal No. 2022-016367, 2 pgs.

* cited by examiner

Log2 Differential Expression

4
2
0
-2
-4 auto fdr>0.1
fdr<0.1

Log2 Differential Expression

4
2
0
-2
-4 lowacl fdr>0.1
fdr<0.1

COMPOSITIONS FOR INTERFERON BLOCKADE AND METHODS OF USING SAME

CROSS-REFERENCE TO RELATED APPLICATIONS

This application claims priority to and benefit of International Application No. PCT/US18/62210 entitled "Compositions for Interferon Blockade and Methods of Using Same," filed Nov. 21, 2018, which claims priority to and benefit of U.S. Provisional Application Ser. No. 62/593,401, filed Dec. 1, 2017, to Sonata Jodele, the contents of which are incorporated in their entirety for all purposes.

BACKGROUND

Transplant-associated thrombotic microangiopathy (TA-TMA) is an important cause of morbidity and mortality after hematopoietic cell transplant (HCT). While applicant has recently showed that complement pathway activation plays significant role in the pathogenesis of TA-TMA and complement blockade with eculizumab improves outcomes in patients with TA-TMA and multi-organ injury, there remains a significant need in the art for treatment of this disease state. In particular, complement blocked with eculizumab improves outcomes in patients with TA-TMA and multi-organ injury, post-transplant survival being improved from 9% to 62% in patients with severe TMA with targeted use of eculizumab (1-3). Despite this improvement, there are patients that do not adequately respond to complement blockade and require novel therapeutic intervention. Further, in addition to a need for treatment for patients with TA-TMA that do not respond to complement blockade, there is a need for treatments for TMA cases refractory to complement blockade, as well as other thrombotic microangiopathies, whether primary or secondary, such as, for example, patients with hemophagocytic lymphohistiocytosis (HLH) who develop symptoms of thrombotic microantiopathy (TMA) in addition to HLH symptoms and who may present with severe multi-organ failure. Further, there exists many other diseases that can present with TMA, such as, for example, transplant associated TMA (TA-TMA) and TMA after solid organ transplant, other, non-transplant, TMAs presenting in variety of vasculitis in rheumatologic diseases, kidney diseases, syndromes associated with liver failure, neurodegenerative disorders, toxic injury (such as spider, snake bite, toxin ingestion, chemotherapy and others), metastatic cancer, sepsis, eclampsia/HELLP syndrome, lupus, hemophagocytic lymphohistiocytosis (HLH), sickle cell disease (SCD) with vaso-occlusive crises, and for which an adequate treatment is not available. Disclosed herein are methods and compositions that address one or more of the aforementioned needs in the art.

BRIEF SUMMARY

Disclosed are compositions that may include one or more inhibitors of interferon activity for the treatment of a disease state, for example, a disorder associated with increased interferon levels such as thrombotic microangiopathy ("TMA"). Also disclosed are methods of treating an individual having a disease state such as thrombotic microangiopathy. Further disclosed are methods of diagnosing an individual with TMA.

BRIEF DESCRIPTION OF THE DRAWINGS

This application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIGS. 1-1D depict change in gene expression between clinical time points. FIG. 1D columns, left to right, are Columns, left to right: upn7_Resolution_TMA, upn27_Resolution_TMA, upn17_Resolution_TMA.

FIG. 2A columns, left to right, are: Columns, left to right: STAT1, HALLMARK_INTERFERON_GAMMA_RESPONSE, HALLMARK_INTERFERON_ALPHA_RESPONSE, ENC_414::K562::INFa6h::STAT2, ENC_410::K562::INFa6h::STAT1, ENC_409::K562::INFa30::STAT1, ENC_413::K562::INFa30::STAT2, p1_TMA_Baseline, p2_TMA_Baseline, p3_TMA_Baseline, p4_TMA_Baseline, p1_TMAResolution_TMA, p2_TMAResolution_TMA, p3_TMAResolution_TMA, p4_TMAResolution_TMA, lowaclp479_TMA_Baseline, lowaclp163_TMA_Baseline, lowaclp451_TMA_Baseline. FIG. 2B show the legends for FIG. 2A.

DETAILED DESCRIPTION

Definitions

Figure 1A:
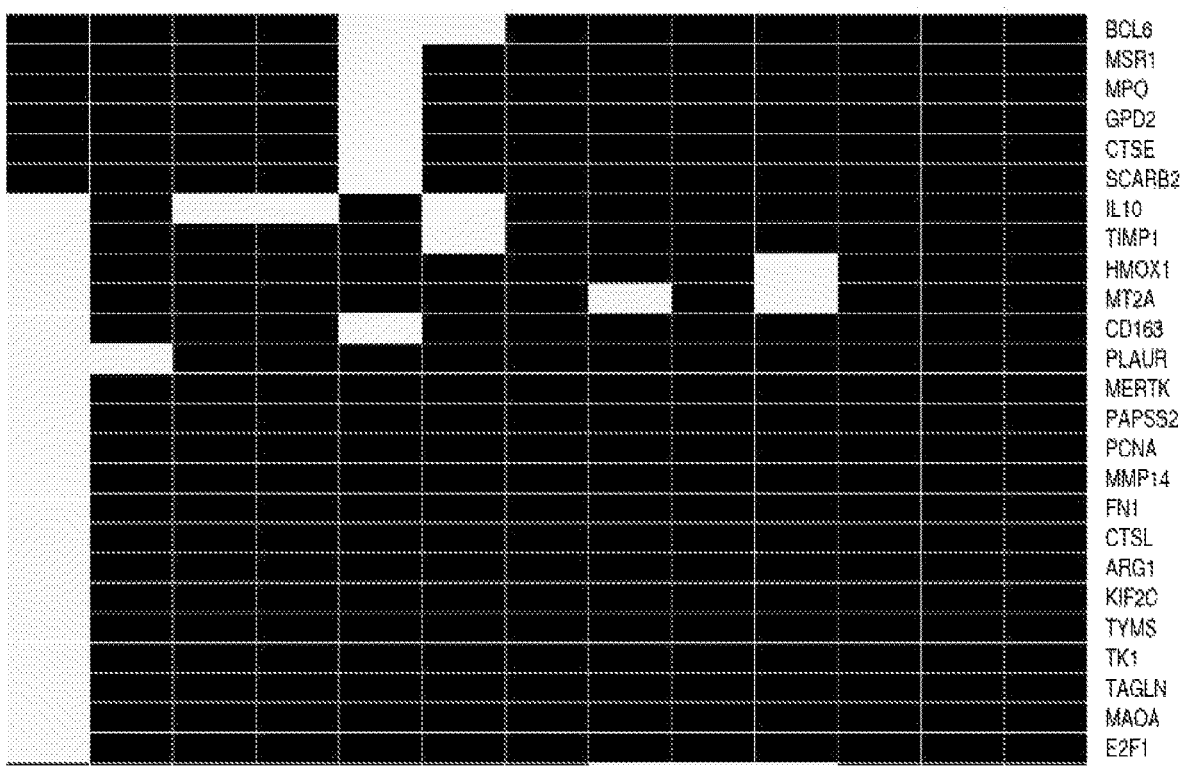
FIGS. 1A and 1B columns, left to right, are: SP1, Complement and coagulation cascades, Systemic lupus erythematosus, Staphyloccus aureus infection, SPI1, STAT1, Osteoclast differentiation, HALLMARK_INTERFERON_GAMMA_RESPONSE, HALLMARK_INTERFERON_ALPHA_RESPONSE, ENC_414::K562::INFa6h::STAT2, ENC_410::K562::INFa6h::STAT1, ENC_409::K562::INFa30::STAT1, ENC_413::K562::INFa30::STAT2.

Unless otherwise noted, terms are to be understood according to conventional usage by those of ordinary skill in the relevant art. In case of conflict, the present document, including definitions, will control. Exemplary methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "antibody or antigen-binding fragment thereof that modulates interferon (IFN) activity" refers to an antibody in its broadest sense capable of modulating IFN activity in a patient, and includes type I and type II IFN. In some aspects, the antibody or antigen-binding fragment thereof inhibits IFN activity. In some aspects, the antibody or antigen-binding fragment thereof is monoclonal. In specific aspects, the antibody or antigen-binding fragment thereof that modulates IFN activity specifically binds to an IFN receptor. In some specific aspects, the antibody or antigen-binding fragment thereof specifically binds to a subunit of an IFN receptor The term "antibody" is used herein in its broadest sense and includes, e.g., monoclonal antibodies, polyclonal antibodies, multivalent antibodies, multispecific antibodies, chimeric antibodies, and humanized antibodies. The term "antibody" includes whole antibodies. The term "antibody" also refers to a protein comprising at least two immunoglobulin heavy (H) chains and two immunoglobulin light (L) chains inter-connected by disulfide bonds, or an antigen binding portion thereof. The term "antibody" also includes "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. Basic antibody structures in vertebrate systems are relatively well understood. For example, methods for producing and screening for specific antibodies using hybridoma technology are routine and known in the art. Briefly, mice can be immunized with an interferon receptor antigen (of any subtype) and once an immune response is detected, e.g., antibodies specific for the desired receptor are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones. Accordingly, monoclonal antibodies can be generated by culturing a hybridoma cell secreting an antibody of the invention wherein the hybridoma is generated by fusing splenocytes isolated from a mouse immunized with an interferon receptor antigen with myeloma cells and then screening the hybridomas resulting from the fusion for hybridoma clones that secrete an antibody able to bind interferon receptor. The disclosed antibodies specifically bind to the desired interferon receptor antigen. Methods for determining whether an antibody binds, including "specifically binds," to an antigen and/or the affinity for an antibody to an antigen are known in the art. For example, the binding of an antibody to an antigen can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA).

There are three general types of interferons: Type I, Type II and Type III interferons. Interferon type I include IFNα and IFNβ. Interferon type II includes IFNγ. Interferon type III signals through a receptor complex consisting of IL10R2 (also called CRF2-4) and IFNLR1 (also called CRF2-12). The term interferon generally refers to Type I, type II and Type III interferons. The terms "type I interferon" or "type I IFN" as used herein refer to members of the type I interferon family of molecules that are ligands for IFNAR1 (i.e., members of the type I interferon family of molecules that are capable of binding IFNAR1). Examples of type I interferon ligands are interferon alpha 1, 2a, 2b, 4, 5, 6, 7, S, 10, 14, 16, 17, 21, interferon beta and interferon omega. The terms "type II interferon" or type II IFN" as used herein refers to members of the type II interferon family of molecules that are ligands for IFNARII (i.e., members of the type II interferon family of molecules that are capable of binding IFNARII). Examples of type II interferon ligands are interferonγ and all subtypes of interferonγ. Interferon blockers include any type of agents capable of blocking any interferon pathway. An interferon blocker may include a small molecule or a biological agent, e.g., an antibody or an antigen binding fragment thereof. If the therapeutic agent is a biological agent, it may be an antibody specific for any Interferon subtype as described herein. For instance, the antibody may be specific for any one of IFNa1, IFNa2, IFNa4, IFNa5, IFNao, IFNa7, IFNa8, IFNa10, IFNa14, IFNa17, IFNa21, IFNI3, or IFNco. Alternatively, the antibody may be specific for any two, any three, any four, any five, any six, any seven, any eight, any nine, any ten, any eleven, any twelve type I IFN of IFNa subtypes. If the antibody is specific for more than one type I IFN subtype, the antibody may be specific for IFNa1, IFNa2, IFN a4, IFNa5, IFNa8, IFNa10, and IFNa21; or it may be specific for IFNa1, IFNa2, IFNa4, IFNa5, IFNa8, and IFNa10; or it may be specific for IFNa1, IFNa2, IFNa4, IFNa5, IFNa8, and IFNa21; or it may be specific for IFNa1, IFNa2, IFNa4, IFNa5, IFNa10, and IFNa21. A therapeutic agent that modulates IFNa activity may neutralize IFNa activity. A type I IFN-mediated disease or disorder can also be treated with antibodies specific for a type I IFN receptor, e.g., IFNAR1. Suitable anti-IFNγ antibodies include the antibodies described in US Patent Application US20180142015A1 and U.S. Pat. No. 7,700,098, which is hereby incorporated by reference in its entirety. Several exemplary antibodies include the antibodies referred to therein as ARC1.2R3P2_A6 ("A6"), ARC1.2R3P2_B4 ("B4"), ARC1.2R3P2_B9 ("B9"), ARC1.2R3P2_C9 ("C9"), ARC1.2R3P2_C10 ("C10"), ARC1.2R3P2_D3 ("D3"), ARC1.2R3P2 D6 ("D6"), ARC1.2R3P2_D8 ("D8"), ARC1.2R3P2_E1 ("E1"), ARC1.2R3P2_F8 ("F8"), ARC1.2R3P2_F9 ("F9"), ARC1.2R3P2_G7 ("G7"), ARC1.2R3P2_G9 ("G9"), and ARC1.2R3P2_G10 ("G10"). The development of antibodies for the described compositions and methods are well-understood and known in the art. Any antibody directed to an interferon as disclosed herein is within the scope of the invention. Exemplary IFN antibodies include, for example, sifalumumab (a fully human mAb against multiple IFN-α subtypes, especially IFN-α6, IFN-2b and IFN-2a), rontalizumab (a human mAb against all 12 IFN-α subtypes, has been trialled in SLE), anifrolumab (is a human mAb against subunit 1 of the IFN-α receptor (IFNAR), and fontolizumab (Type II IFN (IFN gamma)), which are known in the art, and described in, for example, Baker and Isaacs, "Novel therapies for immune-mediated inflammatory diseases: What can we learn from their use in rheumatoid arthritis, spondyloarthritis, systemic lupus erythematosus, psoriasis, Crohn's disease and ulcerative colitis?", Ann Rheum Dis. 2018 February; 77(2):175-187. doi: 10.1136/annrheumdis-2017-211555. Epub 2017 Aug 1.For example, in one aspect, the antibody may be Emapalumab, also known as NI-0501, developed by Novimmune (Switzerland), and which is an anti-IFNγ antibody. Emapalumab is a fully human immunoglobulin G1 anti-interferon gamma (IFNγ) monoclonal antibody which binds and neutralizes IFNγ. Emapalumab binds to both free and receptor (IFNγR1)-bound forms of IFNγ. Emapalumab is a human IgG1 and it retains the characteristics of this immunoglobulin isotype, including the capacity to engage Fcγ receptors and bind complement. https://www.novimmune.com/en/pipeline/emapalumab-ni-0501.html. Similarly, Anifrolumab (also known as MEDI546) is a fully human, effector-null, Ig G1 κ is a monoclonal antibody against the type I interferon (IFN) receptor that inhibits the activity of all type I IFNs (AstraZeneca) is an exemplary antibody within the scope of the invention. A characterization and further details of this antibody is described in Riggs J M, Hanna R N, Rajan B, et al, "Characterisation of anifrolumab, a fully human anti-interferon receptor antagonist antibody for the treatment of systemic lupus erythematosus." Lupus Science & Medicine 2018; 5:e000261. doi: 10.1136/lupus-2018-000261 and Furie, Richard et al. "Anifrolumab, an Anti-Interferon-α Receptor Monoclonal Antibody, in Moderate-to-Severe Systemic Lupus Erythematosus" *Arthritis & rheumatology* (Hoboken, N.J.) vol. 69,2 (2017): 376-386.

The terms "treat" or "treatment" as used herein refer to both therapeutic treatment and prophylactic or preventative measures, wherein the object is to prevent or slow down (lessen) an undesired physiological change or disorder in a subject, such as the progression of an inflammatory disease or condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. The term "treatment" also means prolonging survival as compared to expected survival if not receiving treatment. Those in need of treatment include those already with the condition or disorder as well as those prone to have the condition or disorder or those in which the condition or disorder is to be prevented. Terms such as "treating" or "treatment" or "to treat" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

As used herein, the term "EIS" means an endothelial injury syndrome (endotheliopathies), single or multi-organ injury that occurs due to insult to the vascular endothelium from (but not limited to) inflammatory cytokines and/or complement system activation, and/or toxic agent. TA-TMA, TMA, and cytokine release syndrome (CRS) are examples of EIS presentation. The term includes organ injury resulting from vascular endothelial injury due to a high inflammatory state in patients presenting with transplant associated TMA (TA-TMA) and TMA after solid organ transplant, other, non-transplant, TMAs presenting in variety of vasculitis in rheumatologic diseases, kidney diseases, syndromes associated with liver failure, neurodegenerative disorders, toxic injury (such as spider, snake bite, toxin ingestion, chemotherapy and others), metastatic cancer, sepsis, eclampsia/HELLP syndrome, lupus, hemophagocytic lymphohistiocytosis (HLH), sickle cell disease (SCD) with vaso-occlusive crises. Other EIS syndromes with high inflammatory states likely to benefit from the disclosed compositions and methods include cytokine release storm as a result of chimeric antigen receptor T cell (CART(therapy), veno-occlusive disease of liver (VOD) or also called sinusoidal obstruction syndrome (SOS), diffuse alveolar hemorrhage (DAH), idiopathic pneumonia syndrome (IPS).

As used herein, the term "TA-TMA" means transplant-associated thrombotic microangiopathy.

As used herein, the term "TMA" means thrombotic microangiopathy diagnosed in non-transplant patients.

As used herein, the term "HLH" means: hemophagocytic lymphohistiocytosis.

Transplant-associated thrombotic microangiopathy (TA-TMA) is a significant cause of morbidity and mortality after hematopoietic cell transplant (HCT). TA-TMA belongs to the group of endothelial injury syndrome (EIS, endotheliopathies) resulting from the multifactorial insult to the vascular endothelium that leads to the target organ injury or multi-organ dysfunction syndrome (MODS). Other presentations of EIS include thrombotic microangiopathies (TMAs) occurring in other diseases and conditions unrelated to transplant, cytokine release syndrome (CRS) veno-occlusive disease of liver (VOD) (also referred to as sinusoidal obstruction syndrome (SOS)), diffuse alveolar hemorrhage (DAH), idiopathic pneumonia syndrome (IPS), sepsis and others. The term "endothelial injury syndrome" is used herein to describe organ injury resulting from vascular endothelial injury, as these syndromes are believed to result from endothelial injury by variable insult mechanisms.

In one aspect, disclosed herein are compositions that may comprise one or more inhibitors of interferon activity for the purposes of treating an EIS, or more particularly, a thrombotic microangiopathy ("TMA"), or a disease or disorder presenting with TMA. The interferon activity inhibitor may be selected from an interferon gamma (IFN γ) inhibitor, an interferon alpha inhibitor, an interferon beta inhibitor, or a combination thereof. The inhibitor of interferon activity may be, for example, an antibody or antigen-binding fragment thereof, for example, wherein the inhibitor specifically inhibits an interferon or receptor thereof selected from an interferon gamma (IFN γ) or receptor thereof, an interferon alpha or receptor thereof, an interferon beta or receptor thereof. In one aspect, the inhibitor or combination of inhibitors may be selected from Emapalumab ("NI-0501"), Anifrolumab, Fontolizumab (biopharma), Sifalimumab (interferon alpha monoclonal antibody, "MEDI-545"), Rontalizumab (interferon alpha monoclonal antibody), or a combination thereof.

In one aspect, the disorder treated using the disclosed compositions and methods may be TMA characterized by having lactate dehydrogenase (LDH) elevated above the upper limit of normal for the age of the individual, de novo thrombocytopenia with a platelet count of $50 \times 10^9$/L or a ≥50% decrease in platelet count, de novo anemia with a hemoglobin below the lower limit of normal or anemia requiring transfusion support; and microangiopathic changes defined as the presence of schistocytes in the peripheral blood or histologic evidence of microangiopathy on a tissue specimen, and absence of a coagulopathy and a negative Coombs test.

In a further aspect, the TMA may be characterized by having one or both of 1) a histological TMA diagnosis in tissue biopsy; and 2) four or more markers selected from
 i. LDH above normal value for age,
 ii. schistocytes on peripheral blood smear,
 iii. de novo thrombocytopenia or required platelet transfusions,
 iv. de novo anemia or required RBC transfusions,
 v. hypertension >99% for age (<18 y of age) or 14/90 (>18y of age) or receiving antihypertensive therapy;
 vi. proteinuria >30 mg/dL on random urinalysis ×2 or random urine protein creatine ratio >1 mg/mg; and
 vii. terminal complement activation, characterized by elevated plasma sC5b-9 above normal limit of (>244 ng/ml).

In one aspect, the TMA may be "high risk TMA" characterized by having proteinuria ≥30 mg/dL on random urinalysis ×2 or random urine protein creatine ratio >1 mg/mg; and terminal complement activation, characterized by elevated plasma sC5b-9 above normal limit of (≥244 ng/ml).

Measurements of proteinuria, protein/creatinine ratio and sC5b-9 are all approved clinical tests (CLIA certified) and known in the art. For example, suitable methods are disclosed in Diagnostic and risk criteria for HSCT-associated thrombotic microangiopathy: a study in children and young adults. Jodele S, Davies S M, Lane A, Khoury J, Dandoy C, Goebel J, Myers K, Grimley M, Bleesing J, El-Bietar J, Wallace G, Chima R S, Paff Z, Laskin B L. Blood. 2014 Jul. 24; 124(4):645-53. doi: 10.1182/blood-2014-03-564997. Epub 2014 May 29.PMID:24876561. Proteinuria may be defined as a random urinalysis protein concentration of ≥30 mg/dL and separately examined by random urine protein to creatinine ratio (normal, 0.2 mg/mg, nephrotic range 2 mg/mg). Serum concentration of the soluble membrane attack complex (sC5b-9) at the time of TA-TMA diagnosis and in 20 consecutive time-matched HSCT recipients without TA-TMA may be tested by enzyme-linked immunosorbent assay (normal 72-244 ng/mL).

In certain aspects, the TMA treated using the disclosed compositions and/or methods may be associated with or secondary to a disease or condition selected from post-organ transplant, pregnancy, severe inflammation, cytokine storm syndrome (CRS) due to chimeric antigen receptor T cell (CART) therapy, solid organ transplant, rheumatologic disease, kidney disease, vasculitis in a rheumatologic disease, liver failure, neuro-degenerative disorder, toxic injury (for example, spider bite, snake bite, toxin ingestion, chemotherapy), metastatic cancer, sepsis, eclampsia/HELLP syndrome, lupus, hemophagocytic lymphohistiocytosis (HLH), sickle cell disease (SCD) with vaso-occlusive cirises, veno-occlusive disease of liver (VOD or sinusoidal obstruction syndrome (SOS)), diffuse alveolar hemorrhage (DAH), idiopathic pneumonia syndrome (IPS), multi-organ injury syndrome (MODS), or combinations thereof.

The compositions and methods may further comprise a C5 complement blocker, administered with one or more interferon blocker, whether simultaneously, or alternatively administered with one or more interferon blocker, or administered in close succession to one or more interferon blocker, to an individual in need thereof. The complement blocker may be, in certain aspects, a small molecule or antibody that inhibits complement activity. The complement may be selected from, for example, C1 inhibitor (C1-INH) (Berinert®) (Takahiko Horiuchi and Hiroshi Tsukamoto, "Complement-targeted therapy: development of C5- and C5a-targeted inhibition," Inflammation and Regeneration 201636:11, https://doi.org/10.1186/s41232-016-0013-6. Received: 5 Feb. 2016, accepted: 10 May 2016, published: 3 Jun. 2016), Eculizumab, an anti-C5 monoclonal antibody (Soliris®), Coversin (Akari Therapeutics Plc, Name of Active Ingredient: Recombinant OmCI tick salivary protein), or combinations thereof.

In one aspect, a method of treating an individual having an EIS, or in particular, a TMA is disclosed. The method may comprise the step of administering an inhibitor of interferon activity to said individual, wherein the inhibitor of interferon activity may be selected from an interferon gamma (IFNγ) inhibitor, an interferon alpha inhibitor, an interferon beta inhibitor, or combinations thereof. The inhibitor of interferon activity may be selected from a small molecule, an antibody, or antigen-binding fragment of an antibody, for example wherein the inhibitor specifically inhibits an interferon or receptor thereof selected from an interferon gamma (IFNγ) or receptor thereof, an interferon alpha or receptor thereof, an interferon beta or receptor thereof. Exemplary molecules are described throughout, and include, for example, emapalumab ("NI-0501"), anifrolumab, sifalumumab, rontalizumab, fontolizumab, and combinations thereof.

The method may include treatment of post-transplant TMA, pregnancy associated TMA, TMA secondary to severe inflammation, TMA secondary to cytokine storm syndrome (CRS) due to chimeric antigen receptor T cell (CART) therapy, or combinations thereof. The TMA may be characterized as set forth above or otherwise diagnosed by a medical professional.

The disclosed methods may further comprise the administration of a complement blocker. An exemplary complement blocker is eculizumab. The co-administration includes administering the two or more compounds at the same time, or sequentially, wherein the administration of the one or more than one compounds overlaps or occurs sequentially during the course of treatment for TMA or disease state described herein.

In one aspect, a method of treating an individual suspected of having a disorder associated with increased interferon levels, is disclosed. The method may comprise the steps of a) detecting a level of a marker selected from an interferon or a interferon gamma induced chemokine, preferably wherein said interferon is selected from IFNα, IFNβ, IFNγ, or combinations thereof or wherein said interferon gamma induced chemokine is selected from CXCL9, CXCL10, CXCL11, or combinations thereof, more preferably CXCL9; and b) administering an interferon blocker to the individual when the blood level is increased as compared to a predetermined level.

CXCL9 is also known as C-X-C motif chemokine ligand 9. Tokunaga et al, Cancer Treatment Reviews 63 (2018) 40-47, Bracaglia C, et al. Ann Rheum Dis 2017; 76:166-172. doi:10.1136/annrheumdis-2015-209020, Chemokine (C-X-C motif) ligand 9 (CXCL9) is a small cytokine belonging to the CXC chemokine family that is also known as Monokine induced by gamma interferon (MIG). CXCL9 is a T-cell chemoattractant, which is induced by IFN-γ. It is closely related to two other CXC chemokines called CXCL10 and CXCL11, whose genes are located near the gene for CXCL9 on human chromosome 4. CXCL9, CXCL10 and CXCL11 all elicit their chemotactic functions by interacting with the chemokine receptor CXCR3. CXCL9 is far more sensitive for measuring IFN-g 'activity' than blood IFN levels, and may be considered a measure of choice for interferon gamma activity. Using a sandwich ELISA assay, the normal range of CXCL9 is </=about 121 pg/mL.

In one aspect, the individual suspected of having a disorder associated with increased interferon levels presents with one or more symptoms of TMA.

In one aspect, the individual suspected of having a disorder associated with increased interferon levels is diagnosed with TMA.

In one aspect, the marker level is determined in a blood sample obtained from the individual.

In one aspect, the marker level may be determined in a tissue sample obtained from the individual.

In one aspect, the marker may be free IFNγ, and the predetermined level may be a level of an individual that does not have a disorder associated with increased interferon levels. In one aspect, the predetermined level of free IFNγ is 17 pg/mL as measured using the protocol described in Xu X J, Tang Y M, Song H, M D, Yang S L, Xu W Q, Zhao N, Shi S W, Shen H P, Mao J Q, Zhang L Y, and Pan B H, Diagnostic Accuracy of a Specific Cytokine Pattern in Hemophagocytic Lymphohistiocytosis in Children J Pediatr 2011. The marker may be selected from IFNγ induced chemokines CXCL9, CXCL10, CXCL11, or a combination thereof, wherein the individual may be administered an IFNγ blocker where an increase in said marker is detected as compared to a normal control. The individual may further be administered a complement inhibitor, such as, for example, eculizumab.

In one aspect, a method of diagnosing an individual with TMA is disclosed. The method may comprise the step of detecting IFNγ, CXCL9, CXCL10, CXCL11, or a combination thereof, wherein when said level of IFNγ, CXCL9, CXCL10, CXCL11, or combination thereof is increased compared to a control value, said individual is diagnosed with a disorder selected from TMA, preferably TMA associated with or secondary to a disease or condition selected from post-organ transplant, pregnancy, severe inflammation, cytokine storm syndrome (CRS) due to chimeric antigen receptor T cell (CART) therapy, solid organ transplant, rheumatologic disease, kidney disease, vasculitis in a rheumatologic disease, liver failure, neuro-degenerative disorder, toxic injury (for example, spider bite, snake bite, toxin ingestion, chemotherapy), metastatic cancer, sepsis, eclampsia/HELLP syndrome, lupus, hemophagocytic lymphohistiocytosis (HLH), sickle cell disease (SCD) with vaso-occlusive crises, veno-occlusive disease of liver (VOD or sinusoidal obstruction syndrome (SOS)), diffuse alveolar hemorrhage (DAH), idiopathic pneumonia syndrome (IPS), or combinations thereof.

The dosing protocol for any one or combination of actives may be determined by one of ordinary skill in the art, using known methods. In one aspect, the dosing schedule, particularly where the active is an antibody, may be one similar to that used for emapalumab. For example, emapalumab (a fully human IgG1 monoclonal antibody (mAb) directed against human IFNγ) may be administered by IV over a period of one hour at an initial dose of about 1 mg/kg. A starting dose higher than 1 mg/kg might be used in case of patients who have already been treated with emapalumab at doses higher than 1 mg/kg. Infusions may be performed every 3 days. Dosing frequency adjustments might be needed based on drug pharmacokinetics (PK) for particular patient. Dose adjustments may be guided based on PK data and/or clinical and laboratory response in each patient. Treatment with emapalumab may be continued until a satisfactory response is achieved and maintained for at least 2 weeks. Satisfactory response is determined by improvement in clinical status, improvement or normalization of TA-TMA laboratory parameters and normalization f interferon gamma levels. Suggested therapy course if about 13 weeks, the anticipated duration of treatment can be shortened, although not to less than 4 weeks.

Similarly, the starting dose for either the IFN blocker and/or the complement blocker described herein may be, individually or collectively, about 1 mg/kg, or about 1.5 mg/kg, or about 2 mg/kg, or about 2.5 mg/kg, or about 3 mg/kg, or about 3.5 mg/kg, or about 4 mg/kg, or about 4.5 mg/kg, or about 5 mg/kg. Infusions may be performed daily, or about every other day, or about every 2 days, or about every 3 days, or about every 4 days, or about every 5 days, or about every 6 days, or about every 7 days, or about every 8 days, or about every 8 days, or about every 9 days, or about every 10 days. Administration may be weekly, or every other week, or monthly. The therapy course may be about 2 weeks, or about 3 weeks, or about 4 weeks, or about 5 weeks, or about 6 weeks, or about 7 weeks, or about 8 weeks, or about 9 weeks, or about 10 weeks, or about 11 weeks, or about 12 weeks, or about 13 weeks or more. In one aspect, treatment is about 4 to 20 weeks.

In some embodiments, the active agents provided herein may be provided to an administering physician or other health care professional in the form of a kit. The kit may be, for example, a package which houses a container which contains the one or more active agent(s) in a suitable pharmaceutical composition, and instructions for administering the pharmaceutical composition to a subject. The kit may optionally also contain one or more additional therapeutic agents currently employed for treating the disease states described herein. For example, a kit containing one or more compositions comprising active agents provided herein in combination with one or more additional active agents may be provided, or separate pharmaceutical compositions containing an active agent as provided herein and additional therapeutic agents may be provided. The kit may also contain separate doses of an active agent provided herein for serial or sequential administration. The kit may optionally contain one or more diagnostic tools and instructions for use. The kit may contain suitable delivery devices, e.g., syringes, and the like, along with instructions for administering the active agent(s) and any other therapeutic agent. The kit may optionally contain instructions for storage, reconstitution (if applicable), and administration of any or all therapeutic agents included. The kits may include a plurality of containers reflecting the number of administrations to be given to a subject.

Examples

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Applicant has recently found that complement pathway activation plays a significant role in the pathogenesis of TA-TMA, and that complement blockade with terminal complement blocker eculizumab improves outcomes in patients with TA-TMA presenting with multi-organ injury. Eculizumab is a humanized anti-human C5 monoclonal antibody (Alexion Pharmaceuticals, Inc.), with a human IgG2/IgG4 hybrid constant region, so as to reduce the potential to elicit proinflammatory responses via inhibition of complement component C5. Eculizumab has the trade name Soliris® and is currently approved for treating paroxysmal nocturnal hemoglobinuria ("PNH") and atypical hemolytic uremic syndrome ("aHUS"). (See, e.g., U.S. Patent Publication Number 2012/0237515, and U.S. Pat. No. 6,355,245.) In clinical studies, Applicant improved post-transplant survival from 9% to 62% (72%, updated data) in patients with severe TA-TMA with targeted use of eculizumab (4-6). As noted above, despite this improvement, there are patients with severe TA-TMA who do not adequately respond to complement blockade and who would benefit from discovery of a novel therapeutic target. Applicant has identified a novel targetable endothelial injury pathway for patients with TA-TMA for treatment of TA-TMA and that may be exportable to other thrombotic microangiopathies (primary or secondary) and other endothelial injury syndromes. This may include TA-TMA cases refractory to complement blockade, for example, but also treatment of severe cases at presentation that are life threatening in which both complement blockers and interferon blockers could be used together at initiation (and/or throughout duration) of the therapy.

TMA can present as part of endothelial injury syndromes (EIS) in patients with high inflammatory status due to primary disease or acquired illness that can lead to multi-organ dysfunction syndrome (MODS) and requires prompt intervention to abort lethal complications. TMA and/or EIS is commonly observed in patients with eclampsia/HELLP syndrome, lupus, hemophagocytic lymphohistiocytosis, and a variety of vasculitis in rheumatologic diseases, kidney diseases, syndromes associated with liver failure, degenerative disorders, toxic injury (like spider, snake bite, toxin ingestion, chemotherapy and others), metastatic cancer, sepsis and others.

Applicant performed gene expression analysis studies (RNAseq) in stem cell transplant patients with and without TA-TMA to evaluate for activated and targetable pathways of endothelial injury. Patients were selected with neuroblastoma who underwent autologous stem cell transplant to eliminate additional functional signals that could be introduced by donor cells in allogeneic transplant Clinical data and study specimens were collected as part of an ongoing prospective TA-TMA study. The changes in gene expression were compared in baseline samples, TA-TMA diagnosis (or equivalent time point in patients without TA-TMA) and TA-TMA resolution (or equivalent time point in patients without TA-TMA) between patients with and without TA-TMA. RNAseq was performed by the Genomics, Epigenomics and Sequencing Core in the University of Cincinnati.

Figure 1B:
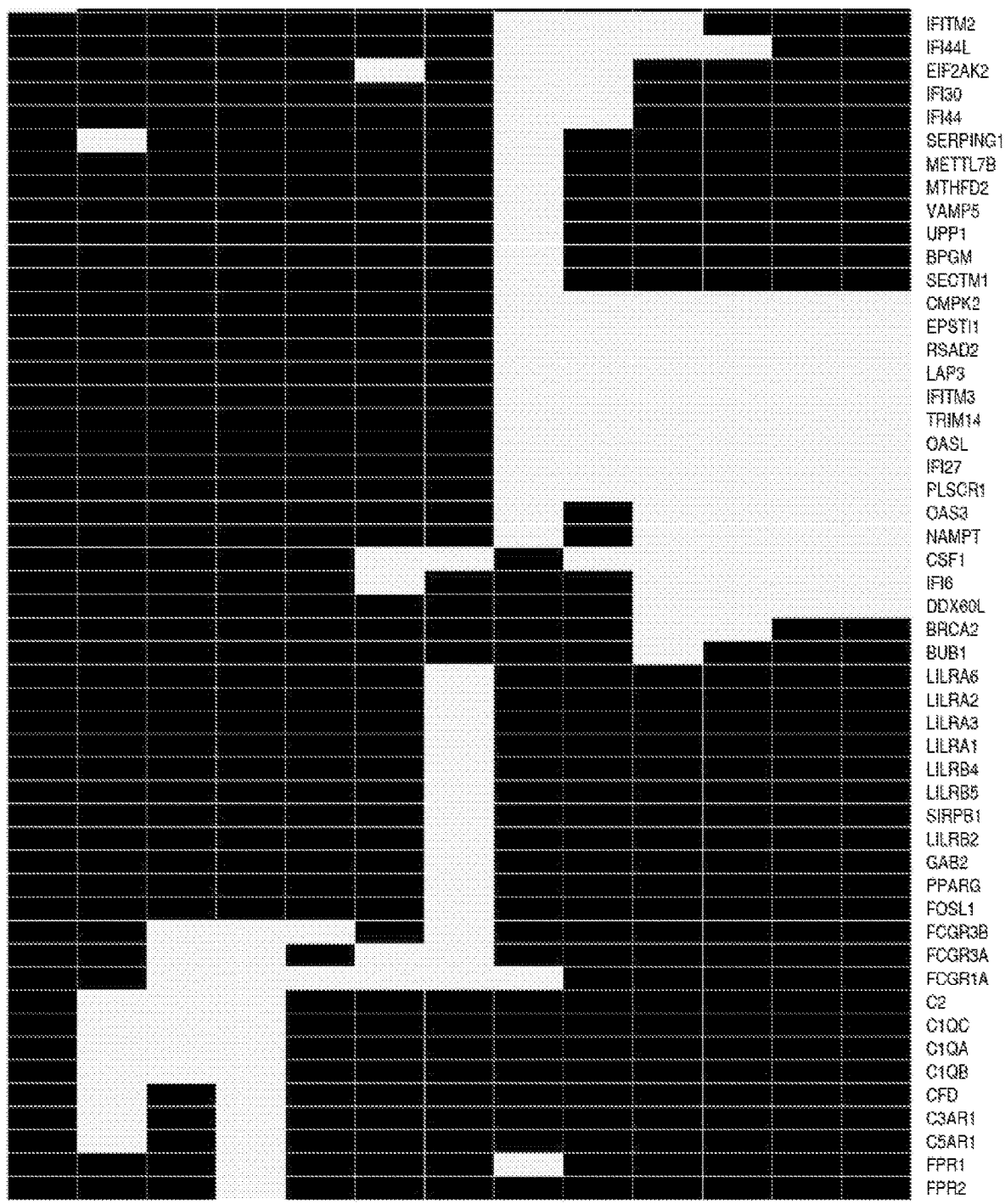
Figure 1C:
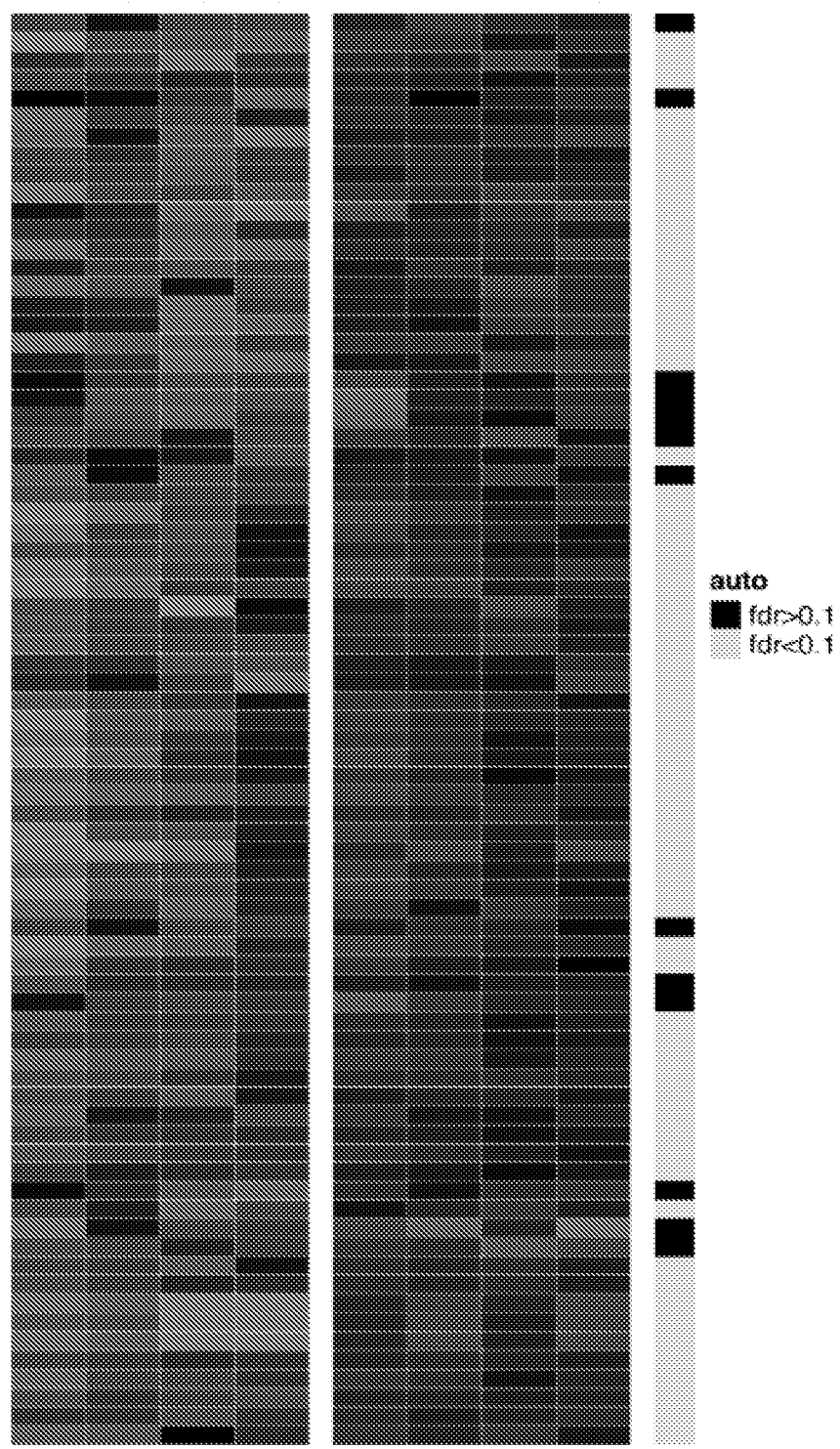
FIG. 1C Columns are, left to right: Columns, left to right: p1_TMA_Baseline, p2_TMA_Baseline, p3_TMA_Baseline, p4_TMA_Baseline, p1_TMAResolution_TMA, p2_TMAResolution_TMA, p3_TMAResolution_TMA, p4_TMAResolution_TMA.
Figure 1D:
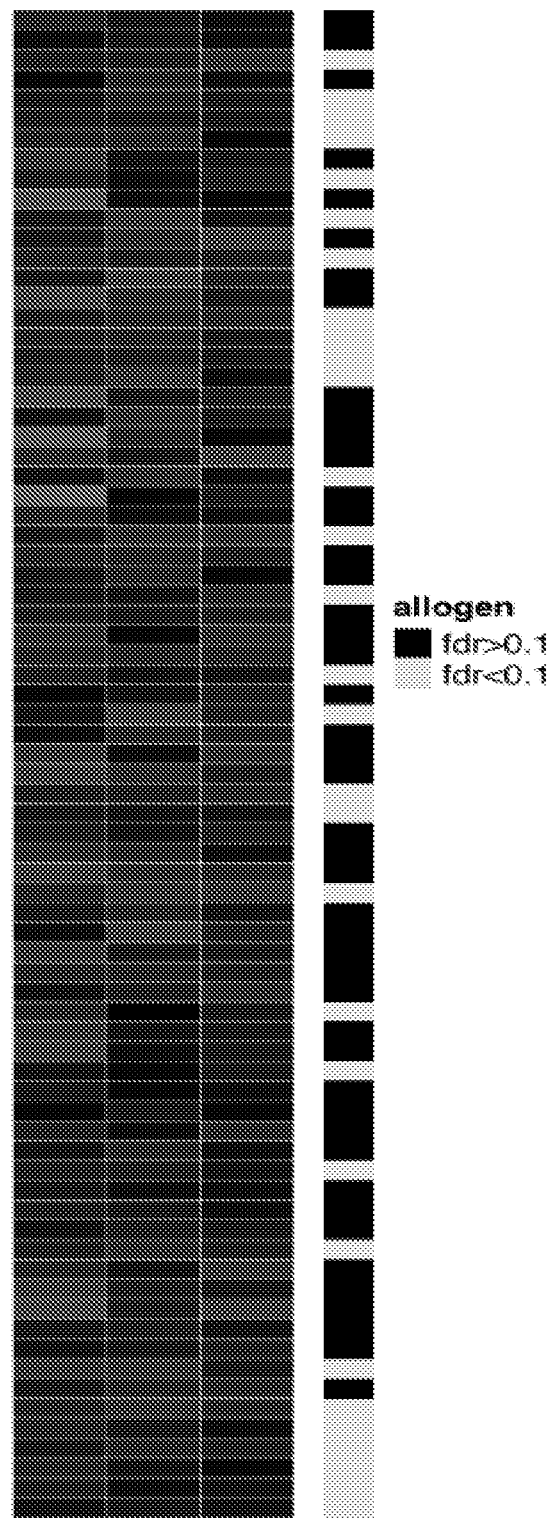
Figure 2A:
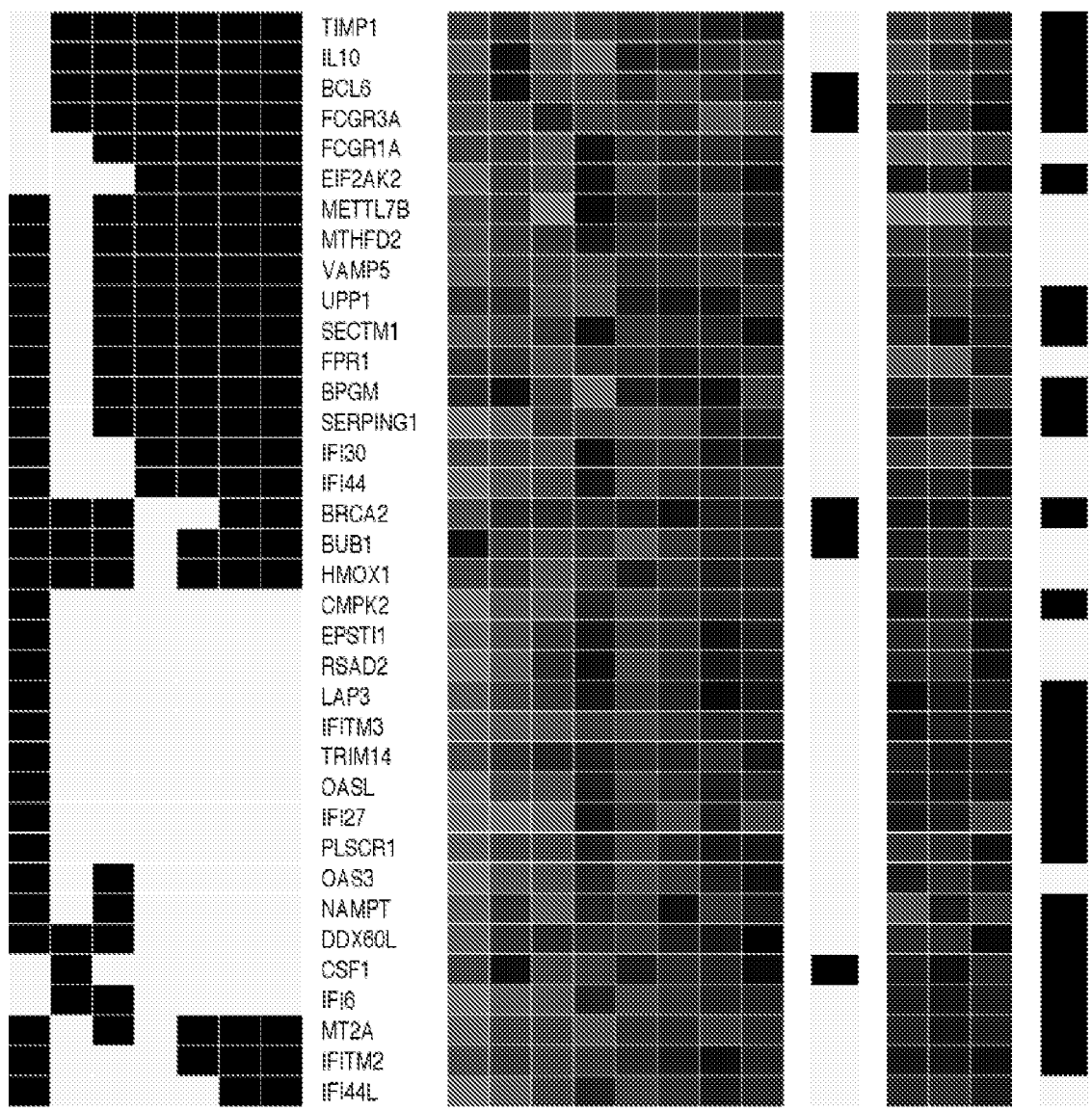
FIGS. 2A and 2B show changes in interferon gene expression profiles in patients with TA-TMA and without TA-TMA. Data indicates that interferon pathways are highly upregulated at TA-TMA diagnosis in stem cell transplant patients with TA-TMA and normalizes after resolution of TA-TMA and not upregulated in patients without TA-TMA at equivalent time points after stem cell transplant.
Figure 2B:
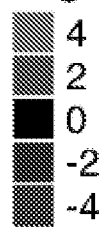
Figure 2B:
Figure 2B:
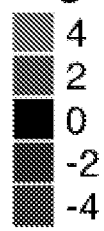
Figure 2B:
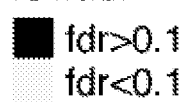

During active TA-TMA, Applicant found significantly marked up-regulation of expression of complement genes, in particular C1Q, the initial component of the complement pathway, essential for classical pathway activation (C1Q C chain elevated 22.8 fold, fdr<$10^{-13}$; B chain elevated 15 fold, fdr<$10^{-11}$; A chain elevated 7.9 fold, fdr<$10^{-7}$). Secondly, during active TA-TMA Applicant found upregulation of other key pathways such as interferons (alpha, beta and gamma) and IL-6 regulated genes, offering the possibility of potential therapies that inhibit these pathways (FIG. 1). The heatmap shown in FIG. 1 illustrates changes in gene expression levels of 76 genes upregulated during active TA-TMA in comparison to baseline (fdr<0.1) in autologous and allogeneic stem cell transplant (HSCT) recipients. Autologous transplant patients with TA-TMA are listed as p1,p2,p3,p4. Allogeneic transplant patients are listed as upn7, upn27, upn17. Times points are listed: at TMA diagnosis ("TMA_Baseline"—this indicates change in gene expression from baseline to the time of TMA diagnosis), TMA resolution ("TMAResolution_TMA" this indicates change in gene expression from TMA diagnosis to resolution of TMA). These genes are members of the key enriched pathways (See, e.g., Kanehisa M, Furumichi M, Tanabe M, Sato Y, Morishima K. KEGG: new perspectives on genomes, pathways, diseases and drugs. Nucleic acids research 2017; 45:D353-D61; Essaghir A, Toffalini F, Knoops L, Kallin A, van Heiden J, Demoulin J B. Transcription factor regulation can be accurately predicted from the presence of target gene signatures in microarray gene expression data. Nucleic acids research 2010; 38:e120; Chen J, Hu Z, Phatak M, et al. Genome-wide signatures of transcription factor activity: connecting transcription factors, disease, and small molecules. PLoS Comput Biol 2013; 9:e1003198; Subramanian A, Tamayo P, Mootha V K, et al. Gene set enrichment analysis: a knowledge-based approach for interpreting genome-wide expression profiles. Proceedings of the National Academy of Sciences of the United States of America 2005; 102:15545-50) listed on the very left side of the figure notably containing elevated expression of complement and coagulation cascades and evidence of an interferon signature. The green bar (fdr<0.1) highlights statistically significant changes in gene expression. The data show notable increased gene expression in inflammatory and complement pathways during active TA-TMA (TMA diagnosis) that are largely resolved at the end of TA-TMA treatment (TMA resolution). A majority (63 out of 76) of the genes elevated during active TA-TMA showed a statistically significant decrease (fdr <0.1) when TMA resolved ("TMA_Resolution" column for HSCT patient. The remaining genes that continued to be elevated were related to proliferation, as is appropriate in recovery from HSCT. All nine genes in the complement and coagulation cascades KEGG pathway that were upregulated during active TA-TMA had resolved at TA-TMA resolution time point in the autologous transplant recipients (p1-4). We wished to determine if similar changes in gene expression occurred after allogeneic transplant so we performed a similar analysis in allogeneic transplant recipients with TA-TMA, comparing gene expression after resolution of TMA with expression during active TA-TMA (patients labeled as "upn7, upn27 and upn17"). The data appear in the last column on the right of the heat map and show a similar pattern of altered expression of complement pathways and interferon with reduction in elevated expression after resolution of TA-TMA. These data demonstrate three important things. Firstly, during active TA-TMA Applicant found very marked up-regulation of expression of complement genes, in particular C1Q, the initial component of the complement pathway, essential for classical pathway activation (C1Q C chain elevated 22.8-fold, fdr<$10^{-13}$; B chain elevated 15-fold, fdr<$10^{-11}$; A chain elevated 7.9-fold, fdr<$10^{-7}$). This finding shows that RNAseq can be effective in illuminating changes in complement expression that can have immediate therapeutic importance. Secondly, during active TA-TMA Applicant found upregulation of other key pathways such as interferon, including seven interferon-regulated complement-related genes, and IL-6 regulated genes, offering the possibility of potential therapies with monoclonal antibodies that inhibit these pathways. Thirdly, the data show that gene expression profiles revert largely to baseline (resting pre-transplant state) when TA-TMA had resolved, indicating that can be reasonably compared to active TA-TMA samples and resolved TA-TMA samples in children receiving allogeneic HCT, without need for a baseline donor sample as used in the autologous HCT recipients. Applicant has performed a similar analysis of 3 children with TMA after allogeneic transplant and seen remarkably similar elevation then resolution of complement pathways. These pathways reverted to normal after resolution of TA-TMA. A very important observation was that interferon pathways were only activated in stem cell transplant patients with severe TA-TMA and were not activated in those without TA-TMA, supporting the concept that high interferon levels contribute to inflammatory endothelial injury causing TMA and not general baseline inflammatory status associated with stem cell transplantation status (FIG. 2). The heatmap shown in FIG. 2 illustrates change in interferon gene expression profiles in patients with TA-TMA and without TA-TMA. Patients with TA-TMA are listed as p1,p2,p3,p4. Times points are listed: Active TA-TMA a TA-TMA diagnosis ("TMA_Baseline"—this indicates change in gene expression from baseline to the time of TA-TMA diagnosis), TA-TMA resolution ("_TMAResolution_TMA" this indicates change in gene expression from TA-TMA diagnosis to resolution of TMA). Patient without TA-TMA were tested at the equivalent post-transplant time to "TMA diagnosis". Patients without TA-TMA are marked as: lowaclp479, lowaclp163, lowaclp451. Data shows broad up-regulation of expression of interferon-regulated genes (interferon alpha, gamma, STAT1 (Signal transducer and activator of transcription 1 (STAT1) is a transcription factor which in humans is encoded by the STAT1 gene. It is a member of the STAT protein family. STAT1 is involved in upregulating genes due to a signal by either type I, type II, or type III interferons.)), including seven interferon-regulated complement-related genes at TA-TMA diagnosis in stem cell transplant recipients with TA-TMA and normalizes after resolution of TA-TMA while those pathways are not upregulated in patients without TA-TMA at equivalent time point post-transplant. Statistical significance between these time points and patient groups are marked as fgr<0.1 (yellow) These data may explain, at least in part, the strong inflammatory component of the typical presentation of TA-TMA, leading to multi-organ injury and may explain lack of immediate and complete response to complement blockade as a single therapy in some patients with severe disease. The RNAseq research by Applicant describes the observations in regard to interferon α, β and γ pathways in patients with neuroblastoma with and without TA-TMA. Applicant's clinical observation describes patients with HLH and activated IFNγ pathway. After initiating prospective screening for TMA, Applicant observed development of severe TMA (not-associated with transplant) leading to multi-organ injury syndrome (MODS) in patients presenting with clinical diagnosis of hemophagocytic lymphohistiocytosis (HLH). HLH is a rare clinical syndrome of excessive immune activation, characterized by signs and symptoms of extreme inflammation, largely driven by IFNγ and other pro-inflammatory cytokines. Recent research demonstrates that high levels of IFNγ plays a pivotal role in the development of HLH. Very high levels of circulating IFNγ were detected in patients with primary (genetic) HLH. In a series of 71 patients monitored from HLH diagnosis to treatment and follow-up, IFNγ levels were above the upper limit of normal (17.3 pg/mL) in all patients, and in particular 53.5% had levels above 1000 pg/mL. It was also reported that IFNγ levels rise early and quickly, and can fall from >5000 pg/mL to normal in 48 hours upon effective treatment of HLH. Clinical diagnostic criteria for HLH include either a molecular HLH diagnosis or five of the following eight criteria: fever, splenomegaly, cytopenias, hypertriglyceridemia and/or hypofibrinogenemia, hemophagocytosis, low or absent NK cell activity, elevated ferritin, and elevated sIL-2 receptor (sIL2R). These criteria are not specific and there is considerable overlap with other conditions. Applicant initially reported a cohort of six patients evaluated for HLH who were also found to have evidence of thrombotic microangiopathy (TMA) with multi-organ injury (Gloude et al, ASBMT abstract 2017). All six patients met clinical HLH criteria. Four patients received HLH-directed therapy prior to arrival, and one patient was not treated following evaluation. HLH genetic studies were done on 3/6 patients with no pathologic mutations identified. All six patients also met clinical criteria for TMA including presence of schistocytes, elevated LDH for age, thrombocytopenia, Coombs negative hemolytic anemia, proteinuria, and hypertension. Additionally, 4/5 patients tested had terminal complement activation (elevated C5b-9). All six patients required ventilator support, 5/6 needed renal replacement therapy, and one needed ECMO. Four patients were treated with eculizumab for TMA and one with therapeutic plasma exchange. Three patients survived: two recovered after eculizumab therapy and one received HCT. Based on these observations we concluded that TMA in in these critically ill patients with HLH is likely initiated by endothelial damage, and the high levels of pro-inflammatory cytokines like IFNγ in conjunction to complement system activation that is a potent cause of endothelial injury in susceptible individuals. HLH can cause liver failure but rarely causes direct renal or pulmonary failure, and TMA in addition to HLH should be considered in children with multi-organ failure.

Applicant therefore has found that interferon blocking agents may be a novel therapeutic option for TA-TMA and likely other thrombotic microangiopathies (TMAs) presenting as part of EIS as standalone therapy or in conjugation with complement blocking agents. CART therapy may cause cytokine release syndrome (CRS). CRS can lead to EIS and also TMA. CRS can range from mild to severe life threatening resulting in multi-organ failure and death. Interferon gamma is one of the inflammatory markers that is elevated during CRS. To date, it is believed that interferon gamma blocker has never before been used in CRS during CART therapy. CRS may result in endothelial injury (EIS), as such, it is believed by Applicant that interferon gamma blockers may be used to treat EIS or TMA during CRS, particularly where CRS becomes life-threatening or may result in multi-organ injury.

Applicant observed HLH patients with documented high blood levels of IFNγ who were receiving IFNγ blocker therapy on Novimmune study who failed to respond to current frontline therapy. Sixteen enrolled patients with diagnosis HLH had prospective monitoring for TMA according to institutional practices. Nine patients with high IFNγ levels had clinical and laboratory evidence of TMA before starting interferon IFNγ therapy. Seven patients resolved TMA and survived. Two of these seven patients resolved TMA on IFNγ blocking therapy alone. TMA in five patients improved on IFNγ blocker, but did not completely resolve. Those patients also showed concurrent complement system activation as measured by elevated blood sC5b-9 and were treated with eculizumab in addition to IFNγ blocker. Eculizumab was added at the start of therapy in two patients and 3 patients received eculizumab 1-4 month after initiating IFNγ blockade. Two of the 9 patients with HLH and TMA died very soon after initiating IFNγ blocking therapy (3 and 4 doses responsively). Both of these patients also had activated complement as measured by elevated blood sC5b-9, but were transferred while being very ill and were not able to neither receive a benefit of IFNγ blocker nor complement blocker.

On the opposite end, thrombotic microangiopathy has been reported as one of iatrogenic side effects of interferon alpha and beta therapy for malignancies and chronic hepatitis. In these patients, interferon therapy is usually discontinued and symptoms are treated with plasma infusion or plasma exchange or administration of steroids or rituximab. In such cases, drug (interferon) required to treat particular disorder is implicated in causing complication as a secondary event and there is no reports of the concept of using interferon blockers in such clinical situations. These observations support Applicant's theory that interferons might be an important druggable targets in primary and secondary TMAs, in particular TMA occurring after stem cell transplantation (TA-TMA) where overall inflammatory response is very prominent and results in multiple organ damage and often death if untreated. For example, there are diseases presenting with EIS and TMA mediated by interferon and complement pathways together, such as that described in "Degos Disease: A C5b-9/Interferon-α-Mediated Endotheliopathy Syndrome" Magro et al, Am J Clin Pathol 2011; 135:599-610. Degos disease is a distinct vascular injury syndrome whereby a dysregulated interferon-α response in concert with membranolytic attack complex deposition may contribute to the unique vascular changes. Thus, it is believed that complement and interferon pathway activation together causes severe endothelial injury leading to TMA and EIS and will therefore likely benefit from both types of inhibition as described by Applicant.

In view of Applicant's observations, it is believed by Applicant that interferon pathway activation plays a role in endothelial injury syndromes (EIS), especially in TA-TMA and non-transplant associated TMA pathogenesis. Significant interferon activation contributes to severe organ injury for what clinical intervention will likely result in TMA or TA-TMA resolution. Interferon levels can be clinically detected and monitored to determine which patients will, or are likely to, benefit from interferon blockade. Interferon blockers may be used as novel therapeutic option either as a single agent or in conjunction with other agents like complement blocking agents for endothelial injury syndromes (endotheliopathies) presenting as TA-TMA, non-transplant TMA occurring in other illnesses, cytokine release syndromes (CRS) and other diseases or syndromes leading to or associated with endothelial injury. Personalized dosing may be determined for certain endotheliopathies, in particular, for patients with TA-TMA undergoing transplant and other TMAs in which the inflammatory process is likely to be very active. Monoclonal antibodies are "used up" in the body based on disease activity and disease "targets" they need to block, thereby potentially requiring increased administration depending on severity. Required dosing may be established using PK/PD studies, the methods for which are known in the art.

Interferon blockers may be used in other thrombotic microangiopathies (TMA), primary or secondary including, but not limited to aHUS, TTP, HELLP syndrome, eclampsia and other interferon driven diseases, lupus erythematosus (SLE), HLH, sickle cell disease (SCD) vaso-occlusive crises/acute chest, and vasculitic disorders that presents with TMA. Interferon blockers, in particular, an IFNγ blocker, may be used to ameliorate endothelial injury and cytokine release syndrome (CRS) and TMA associated with chimeric antigen receptor-modified (CAR) T cells cell therapies. (CAR) T cells have produced impressive antitumor responses in patients with refractory B-cell malignancies but is often associated with cytokine release syndrome (CRS) and severe endothelial injury. IFNγ is one of the cytokines elevated in patients with clinically significant CRS resulting in endothelial damage. These novel (CAR)T therapies will be widely used in adult and children and will provide large market for drugs (like interferon blockers) alleviating side effects of CRS and endothelial injury and preventing multi-organ injury.

Currently, an anti-interferon Gamma (Anti-IFNγ) Monoclonal Antibody emapalumab (NI-0501), available from Novimmune is in pediatric study for patients with HLH.

Applicant has further observed activation of other interferon pathways (like alpha and beta) in patients with endotheliopathies, including TA-TMA. Anifrolumab is a monoclonal antibody specific to the type I interferon (IFN) receptor that inhibits the activity of all type I IFNs (available from AstraZeneca), and which has been studied in lupus. Anifrolumab is a human mAb against subunit 1 of the IFN-αR1 receptor (IFNAR) which, in a recent phase IIb clinical trial of 305 patients with SLE, showed efficacy versus placebo both for global and organ-specific disease activity. Furie R, Khamashta M, Merrill J T, et al. Anifrolumab, an Anti-Interferon-receptor monoclonal antibody, in Moderate-to-Severe systemic lupus erythematosus. Arthritis Rheumatol 2017; 69:376-86. Development of other interferon alpha or beta blockers may be used to treat endotheliopathies presenting with elevated interferon levels. Other interferon blockers include sifalumumab, rontalizumab, anifrolumab and fontolizumab.

The methods may comprise interferon blocker(s) either as monotherapy or combined with a complement blocking agent based on clinical presentation of severe endotheliopathies and type of interferon elevated (Type I (interferon α,β)

and Type II (interferon γ). Interferon blockers may be used to reverse interferon therapy induced TMA and endothelial injury syndrome.

The following method of detecting CXCL9 and CXCL10 lab levels may be used to carry out the disclosed methods:

CHLA lab: a normal CXCL9 is <121 pg/mL clinically.

As per the ELISA kit, CXCL9 normal values are:

| Sample Type | Mean (pg/mL) | Range (pg/mL) |
|---|---|---|
| Serum (n = 40) | 64.4 | * ND-199 |
| EDTA plasma (n = 23) | 56.7 | ND-179 |
| Heparin plasma (n = 25) | 62.0 | ND-209 |

* ND = not detected

As per the ELISA kit, CXC110 normal values are:

| Sample Type | Mean (pg/mL) | Range (pg/mL) |
|---|---|---|
| Serum (n = 60) | 89 | 38-361 |
| EDTA plasma (n = 35) | 96 | 47-382 |
| Heparin plasma (n = 35) | 110 | 52-450 |

The range on the CXCL9 ELISA kit is 31.3-2000 pg/mL and for CXCL10 is 7.8-500 pg/mL. CXCL10 is a surrogate for IFN alpha and beta, and IFN gamma and (to a certain extent), while CXCL9 is quite specific for IFN gamma.

REFERENCES

Billiau A. Interferon-gamma: biology and role in pathogenesis. Adv. Immunol. 1996; 62:61-130.

Schoenborn J R, Wilson C B. Regulation of interferon-gamma during innate and adaptive immune responses. Adv. Immunol. 2007; 96:41-101.

Zhang S Y, Boisson-Dupuis S, Chapgier A et al. Inborn errors of interferon (IFN)-mediated immunity in humans: insights into the respective roles of IFN-alpha/beta, IFN-gamma, and IFN-lambda in host defense. Immunol. Rev. 2008; 226:29-40.

Jodele S, Davies S M, Lane A, Khoury J, Dandoy C*, Goebel J, Myers K, Grimley M, Bleesing J, El-Bietar J*, Wallace G, Chima R S, Paff Z, Laskin B L*. Diagnostic and risk criteria for HSCT-associated thrombotic microangiopathy: a prospective a prospective study in children and young adults. Blood. 2014 Jul. 24; 124(4):645-53. PMID: 24876561

Jodele S, Zhang K, Zou F*, Laskin B*, Dandoy C E*, Myers K C, Lane A, Meller J, Medvedovic M, Chen J, Davies S M. The genetic fingerprint of susceptibility for transplant associated thrombotic microangiopathy. Blood. 2016 Feb. 25; 127(8):989-96. PMID: 26603840

Jodele S, Fukuda T, Mizuno K*, Vinks A A, Laskin B L*, Goebel J, Dixon B P, Chima R S, Hirsch R, Teusink A, Lazear D, Lane A, Myers K C, Dandoy C E* and Davies S M. Variable eculizumab clearance requires pharmacodynamic monitoring to optimize therapy for thrombotic microangiopathy after hematopoietic stem cell transplantation. Biol Blood Marrow Transplant. 2016 February; 22(2): 307-15. PMID: 26456258

Pachlopnik S J, Ho C H, Chretien F et al. Neutralization of IFNγ defeats haemophagocytosis in LCMV-infected perforin- and Rab27a-deficient mice. EMBO Mol. Med. 2009; 1:112-124.

Baghbanian S M, Moghadasi A N. Thrombotic microangiopathy associated with interferon-beta treatment in patients with multiple sclerosis. Iran J Neurol. 2018 Apr. 4; 17(2):89-90. No abstract available. PMID: 30210735

Jia H, Thelwell C, Dilger P, Bird C, Daniels S, Wadhwa M Endothelial cell functions impaired by interferon in vitro: Insights into the molecular mechanism of thrombotic microangiopathy associated with interferon therapy. Thromb Res. 2018 March; 163:105-116. doi: 10.1016/j.thromres.2018.01.039. Epub 2018 Feb. 6. PMID:29407621

Allinovi M, Cirami C L, Caroti L, Antognoli G, Farsetti S, Amato M P, Minetti E E. Thrombotic microangiopathy induced by interferon beta in patients with multiple sclerosis: three cases treated with eculizumab. Clin Kidney J. 2017 October; 10(5):625-631. doi: 10.1093/ckj/sfw143. Epub 2017 Feb. 16. PMID: 28980667

Magro CM1, Poe J C, Kim C, Shapiro L, Nuovo G, Crow M K, Crow Y J. Degos disease: a C5b-9/interferon-α-mediated endotheliopathy syndrome. Am J Clin Pathol. 2011 April; 135(4):599-610. doi: 10.1309/AJCP66QIMFARLZKI.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method of treating an individual having thrombotic microangiopathy (TMA) due to hemophagocytic lymphohistiocytosis (HLH), comprising administering emapalumab to said individual.

2. The method of claim 1, wherein said TMA is post-transplant TMA, pregnancy associated TMA, TMA secondary to severe inflammation, TMA secondary to cytokine storm syndrome (CRS) due to chimeric antigen receptor T cell (CART) therapy, or combinations thereof.

3. The method of claim 1, wherein said TMA is characterized by having one or both of
   a. a histological TMA diagnosis in tissue biopsy; and
   b. four or more markers selected from
      i. lactate dehydrogenase (LDH) above normal value for age,
      ii. schistocytes on peripheral blood smear,
      iii. de novo thrombocytopenia or required platelet transfusions,
      iv. de novo anemia or required red blood cell (RBC) transfusions,
      v. hypertension >99% for age (<18 years of age) or 14/90 (≥18 years of age) or receiving antihypertensive therapy;
      vi. proteinuria ≥30 mg/dL on random urinalysis ×2 or random urine protein creatinine ratio >1 mg/mg; and
      vii. terminal complement activation, characterized by elevated plasma sC5b-9 above normal limit of (≥244 ng/ml).

4. The method of claim 1, wherein said TMA is high risk TMA and is characterized by having proteinuria ≥30 mg/dL on random urinalysis ×2 or random urine protein creatinine ratio >1 mg/mg; and terminal complement activation, characterized by elevated plasma sC5b-9 above normal limit of (≥244 ng/ml).

5. The method of claim 1, further comprising the step of administering a complement blocker.

6. A method of treating an individual suspected of having thrombotic microangiopathy (TMA) due to HLH, comprising
   a. detecting a level of a marker selected from an interferon or an interferon gamma (IFNγ) induced chemokine, wherein said interferon gamma induced chemokine is selected from CXCL9, CXCL10, CXCL11, or combinations thereof; and
   b. administering emapalumab to said individual when a blood level is increased as compared to a predetermined level.

7. The method of claim 6 wherein said individual further presents with one or more symptoms of TMA.

8. The method of claim 6 wherein said individual is diagnosed with TMA.

9. The method of claim 6 wherein said marker level is determined in a blood sample obtained from said individual.

10. The method of claim 6 wherein said marker level is determined in a tissue sample obtained from said individual.

11. The method of claim 6 wherein said marker is free IFNγ, and said predetermined level is a level of an individual that does not have a disorder associated with increased interferon levels.

12. The method of claim 11, wherein said predetermined level is 17 pg/mL.

13. The method of claim 6 wherein said marker is selected from IFNγ induced chemokines CXCL9, CXCL10, CXCL11, or a combination thereof, wherein said individual is administered an IFNγ blocker where an increase in said marker is detected as compared to a normal control.

14. The method of claim 6, further comprising administering a complement inhibitor.

15. The method of claim 14, wherein said complement inhibitor is eculizumab.

\* \* \* \* \*